(12) United States Patent
Regan et al.

(10) Patent No.: US 6,228,881 B1
(45) Date of Patent: May 8, 2001

(54) AROMATIC HETEROCYCLIC COMPOUNDS AND THEIR USE AS ANTI-INFLAMMATORY AGENTS

(75) Inventors: John R. Regan, Larchmont, NY (US); Pier F. Cirillo, Woodbury, CT (US); Eugene R. Hickey, Danbury, CT (US); Neil Moss, Ridgefield, CT (US); Charles L. Cywin, Bethel, CT (US); Christopher Pargellis, West Redding, CT (US); Thomas A. Gilmore, Middlebury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/461,446

(22) Filed: Dec. 14, 1999

Related U.S. Application Data

(62) Division of application No. 09/181,743, filed on Oct. 29, 1998.
(60) Provisional application No. 60/064,102, filed on Nov. 3, 1997.

(51) Int. Cl.$^7$ ......................... A61K 31/38; C07D 409/00
(52) U.S. Cl. .............................................. 514/432; 549/60
(58) Field of Search ................................ 549/60; 514/432

*Primary Examiner*—Amelia Owens
(74) *Attorney, Agent, or Firm*—Robert P. Raymond; Anthony P. Bottino; Alan R. Stempel

(57) ABSTRACT

Novel aromatic heterocyclic compounds inhibit cytokines production involved in immunoregulation and inflammation such as interleukin-1 and tumor necrosis factor production. The compounds are therefore useful in pharmaceutic compositions for treating diseases or pathological conditions involving inflammation such as chronic inflammatory diseases.

11 Claims, No Drawings

AROMATIC HETEROCYCLIC COMPOUNDS AND THEIR USE AS ANTI-INFLAMMATORY AGENTS

RELATED APPLICATIONS

This application is a divisional of U.S. application Ser. No. 09/181,743 filed Oct. 29, 1998 which claims benefit to U.S. provisional application Ser. No. 60/064,102, filed on Nov. 3, 1997.

TECHNICAL FIELD OF THE INVENTION

The invention relates to aromatic heterocyclic compounds which inhibit the release of inflammatory cytokines such as interleukin-1 and tumor necrosis factor from cells and are thus useful for treating diseases and pathological conditions involving inflammation such as chronic inflammatory disease. The invention also relates to processes for preparing such compounds and pharmaceutical compositions comprising them.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J Invest. Med.* 43: 28–38). An important and accepted therapeutic approach for potential drug intervention in these diseases is the reduction of proinflammatory cytokines such as TNF (also referred to in its secreted, cell-free form termed TNFα) and IL-1β. A number of anti-cytokine therapies are currently in clinical trials. Efficacy has been demonstrated with a monoclonal antibody directed against TNF in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitis shows dependence on IL-1. Some of this damage may be mediated through other effectors such as prostaglandins and thromboxanes. Il-1 can effect this process by controlling the level of both cyclooxygenase II and inducible nitric oxide synthetase expression (McDaniel et al., 1996, *Proc Soc Exp Biol Med.* 211, 24). Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is due to a sustained elevation of IL-1 (Holden, et al., 1995, *Med Hypootheses* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The distructive process associated with peridontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. TNFα has also been implicated in cachexia and muscle degradation, associated with HIV infection (Lahdiverta et al., 1988, *Amer. J Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. In consequence, IL-8 has a role in acute respiratory response syndrome (ARDS) and in cerebral reperfusion injury (Matsumoto, et al., 1997, *Journal of Leukocyte Biology* 62: 581). Blocking antibodies against IL-8 have demonstrated a role for IL-8 in the neutrophil associated tissue injury in acute inflammation (Harada et al., 1996: *Molecular Medicine Today* 2: 482). Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dememtia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al, 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J Med Chem.*, 41, 1050). GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including bum-wound healing, skin-graft resolutions as well as cytostatic and radiotherapy induced mucositis (Masucci, 1996, *Medical Oncology* 13: 149). GM-CSF also appears to play a role in the replication of human immuno-deficiency virus (HIV) in cells of macrophage lineage with relevance to AIDS therapy (Crowe et al., 1997, *Journal of Leukocyte Biology* 62: 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al, 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). A reduced production of IFN γ is associated with onset of allergic disease in infants (Warner et al., 1997, *Pediatr Allergy Immunol.* 8, 5). Allergic subjects produce mRNA specific for IFN γ following challenge with Vespula venom (Bonay, et al., 1997, *Clin Exp ImmunoL* 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al, 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 Suppl 2, 43). Treatment of patients with IFN has demonstrated efficacy in a number of diseases including Behcet's disease which is a multisystem vasculitis. Interestingly in a small patient study for uveitis treatment with IFN γ was essentially ineffective (Kotter, et al., 1996, *Ger J Ophthalmol.* 5, 92). A number of cancers can be treated with IFN γ, this includes the treatment of multiple myeloma. Much of the effect is apparently dependent on IL-6 which is a central myeloma growth factor (Palumbo et al., 1995, *Leuk Lymphoma* 18, 215). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF DESCRIPTION OF THE INVENTION

The invention provides novel compounds which inhibit the release of inflammatory cytokines such as interleukin-1 and tumor necrosis factor from cells and which are thus useful for treating diseases and pathological conditions involving inflammation such as chronic inflammatory disease.

DETAILED DESCRIPTION OF THE INVENTION

In its broadest generic aspect, the invention provides novel compounds of the formula I

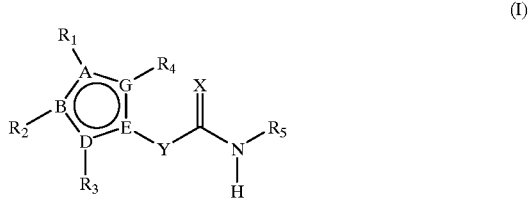

wherein:
A is C or N;
B is C, N, O or S;
D is C, N or S;
E is C or N;
G is C, S or N;
X is S, O or $NR_6$;
Y is $CHR_7$ or N—H;
$R_1$ is selected from the group consisting of:
(a) $C_{3-10}$ branched alkyl, which is optionally partially or fully halogenated, and optionally substituted with one to three phenyl, naphthyl or heteroaryl groups (each such heteroaryl group being independently selected from pyridinyl, pyrimidinyl, pyrazinyl, pyridazinyl, pyrrolyl, imidazolyl, pyrazolyl, thienyl, furyl, isoxazolyl and isothiazolyl), each such phenyl, naphthyl or heteroaryl group being substituted with 0 to 5 groups selected from halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, aminocarbonyl and di($C_{1-3}$) alkylaminocarbonyl;
(b) a cycloalkyl group selected from cyclopropyl, cyclobutyl, cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups, or an analog of such cycloalkyl group wherein instead of one to three ring methylene groups there are groups independently selected from O, S, CHOH, >C=O, >C=S and NH;
(c) $C_{3-10}$ branched alkenyl which is optionally partially or fully halogenated, and which is optionally substituted with one to three groups independently selected from $C_{1-5}$ branched or unbranched alkyl, phenyl, naphthyl or heteroaryl, with each such heteroaryl group being independently selected from pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heteroaryl group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, cyano, $C_{1-3}$ alkyloxy which is optionally partially or fully halogenated, aminocarbonyl and mono- or di($C_{1-3}$)alkylaminocarbonyl;

(d) a cycloalkenyl group selected from cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

(e) cyano; and, (f) an alkoxy carbonyl group selected from methoxycarbonyl, ethoxycarbonyl and propoxycarbonyl;

$R_2$ is selected from the group consisting of the following, when B is a carbon atom or an amino nitrogen: hydrogen, $C_{1-6}$ branched or unbranched alkyl which is optionally partially or fully halogenated, acetyl, benzoyl and phenylsulfonyl;

$R_3$ is selected from the group consisting of the following, when D is a carbon atom or an amino nitrogen:

a) phenyl, naphthyl and heteroaryl (wherein said heteroaryl group is selected from pyridinyl, pyrimidinyl, pyrazinyl, pyridazinyl, pyrrolyl, imidazolyl, pyrazolyl, thienyl, furyl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl), wherein such phenyl, naphthyl or heteroaryl group is optionally substituted with one to five groups independently selected from $C_{1-6}$ branched or unbranched alkyl, phenyl, naphthyl, heteroaryl selected from the group set forth immediately above, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, hydroxy, cyano, $C_{1-3}$ alkyloxy which is optionally partially or fully halogenated, phenyloxy, naphthyloxy, hetearyloxy wherein the heteroaryl moiety is selected from the group set forth above in this subparagraph, nitro, amino, mono- or di-($C_{1-3}$)alkylamino, phenylamino, naphthylamino, heteroarylamino wherein the heteroaryl moiety is selected from the group set forth above in this subparagraph, aminocarbonyl, a mono- or di-($C_{1-3}$)alkyl aminocarbonyl, $C_{1-4}$ branched or unbranched alkyl oxycarbonyl, $C_{1-5}$ alkylcarbonyl $C_{1-4}$ branched or unbranched alkyl, amino $C_{1-5}$ alkyl, mono- or di-($C_{1-3}$)alkylamino($C_{1-5}$)alkyl, aminosulfonyl, di-($C_{1-3}$)alkylaminosulfonyl;

b) fused aryl (selected from benzocyclobutanyl, indanyl, indenyl, dihydronaphthyl, tetrahydronaphthyl, benzocycloheptanyl and benzocycloheptenyl), and fused heteroaryl (selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene), wherein the fused aryl or fused heteroaryl ring is substituted with 0 to 3 groups independently selected from phenyl, naphthyl and heteroaryl (wherein each such heteroaryl is selected from pyridinyl, pyrimidinyl, pyrazinyl, pyridazinyl, pyrrolyl, imidazolyl, pyrazolyl, thienyl, furyl, isoxazolyl and isothiazolyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heteroaryloxy (wherein the heteroaryl moiety is selected from the group set forth above in this subparagraph), nitro, amino, mono- or di-($C_{1-3}$)alkylamino, phenylamino, naphthylamino, heteroarylamino (wherein the heteroaryl moiety is selected from the group set forth above in this subparagraph), aminocarbonyl, a mono- or di-($C_{1-3}$)alkyl aminocarbonyl, $C_{1-4}$ branched or unbranched alkyl oxycarbonyl, $C_{1-5}$ alkylcarbonyl $C_{1-4}$ branched or unbranched alkyl, amino $C_{1-5}$ alkyl, mono- or di-($C_{1-3}$)alkylamino($C_{1-5}$)alkyl, aminosulfonyl, di-($C_{1-3}$)alkylaminosulfonyl;

c) a cycloalkyl group selected from cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups;

d) a cycloalkenyl group selected from cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups; and, e) acetyl, benzoyl and phenylsulfonyl;

or $R_1$ and $R_2$ taken together may optionally form a fused phenyl or pyridinyl ring, or $R_2$ and $R_3$ taken together may optionally form a fused phenyl or pyridinyl ring, $R_4$ is selected from the following, when G is a carbon atom or an amino nitrogen: hydrogen and $C_{1-6}$ branched or unbranched alkyl which is optionally partially or fully halogenated;

$R_5$ is selected from the group consisting of:

a) phenyl, naphthyl and heteroaryl (wherein such heteroaryl is selected from pyridinyl, pyrimidinyl, pyrazinyl, pyridazinyl, pyrrolyl, imidazolyl, pyrazolyl, thienyl, furyl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl), wherein such phenyl, naphthyl or heteroaryl group optionally bears one to five groups selected from phenyl, naphthyl and heteroaryl (wherein each such heteroaryl moiety is independently selected from the group defined above in this subparagraph), $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, halo, cyano, $C_{1-3}$ alkyloxy which is optionally partially or fully halogenated, phenyloxy, naphthyloxy, nitro, amino, mono- or di-($C_{1-3}$) alkylamino, phenylamino, naphthylamino, aminocarbonyl, mono- or di-($C_{1-3}$) alkylaminocarbonyl, amino($C_{1-5}$)alkyl or alkenyl, di-($C_{1-3}$)alkylamino($C_{1-5}$)alkyl or alkenyl, phenylamino ($C_{1-3}$)alkyl or alkenyl, naphthylamino($C_{1-3}$)alkyl or alkenyl, phenylamido($C_{1-3}$)alkyl or alkenyl, naphthylamido($C_{1-3}$)alkyl or alkenyl, phenyl($C_{1-5}$) alkyl or alkenyl and naphthyl($C_{1-5}$)alkyl or alkenyl;

b) fused aryl (selected from benzocyclobutanyl, indanyl, indenyl, dihydronaphthyl, tetrahydronaphthyl, benzocycloheptanyl and benzocycloheptenyl), and fused heteroaryl (selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene), wherein the fused aryl or fused heteroaryl ring bears 0 to 3 groups selected from phenyl, naphthyl, heteroaryl (wherein such heteroaryl is selected from pyridinyl, pyrimidinyl, pyrazinyl, pyridazinyl, pyrrolyl, imidazolyl, pyrazolyl, thienyl, furyl, isoxazolyl and isothiazolyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy, nitro, amino, mono- or di-$(C_{1-3})$ alkylamino, phenylamino, naphthylamino, aminocarbonyl, mono- or di-$(C_{1-3})$ alkylaminocarbonyl, amino$(C_{1-5})$alkyl or alkenyl, di-$(C_{1-3})$alkylamino$(C_{1-5})$alkyl or alkenyl, phenylamino$(C_{1-3})$alkyl or alkenyl, naphthylamino$(C_{1-3})$alkyl or alkenyl, phenylamido$(C_{1-3})$alkyl or alkenyl, naphthylamido$(C_{1-3})$alkyl or alkenyl, phenyl$(C_{1-5})$ alkyl or alkenyl and naphthyl$(C_{1-5})$alkyl or alkenyl;

c) cycloalkyl selected from cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups;

d) cycloalkenyl selected from cyclopentenyl, cyclohexenyl, cyclohexadienyl, cycloheptenyl, cycloheptadienyl, bicyclohexenyl and bicycloheptenyl, which cycloalkenyl group is optionally partially or fully halogenated and which is optionally substituted with one to three $C_{1-3}$ alkyl groups; and e) phenyl($C_{1-5}$ branched or unbranched)alkyl, and naphthyl($C_{1-5}$ branched or unbranched)alkyl, wherein the phenyl or naphthyl ring is substituted with 0 to 5 groups selected from the group consisting of phenyl, naphthyl, heteroaryl (selected from pyridinyl, pyrimidinyl, pyrazinyl, pyridazinyl, pyrrolyl, imidazolyl, pyrazolyl, thienyl, furyl, isoxazolyl and isothiazolyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy or heteroaryloxy (wherein the heteroaryl moiety is as defined above in this subparagraph);

$R_6$ is hydrogen, cyano or $C_{1-6}$ branched or unbranched alkyl which is optionally partially or fully halogenated; and, $R_7$ is hydrogen or $C_{1-6}$ branched or unbranched alkyl, which is optionally partially or fully halogenated.

In a somewhat preferred generic aspect, the invention comprises compounds of the above formula I, wherein:

the heterocyclic moiety

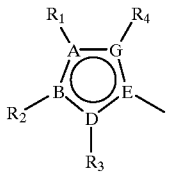

is selected from the group consisting of:

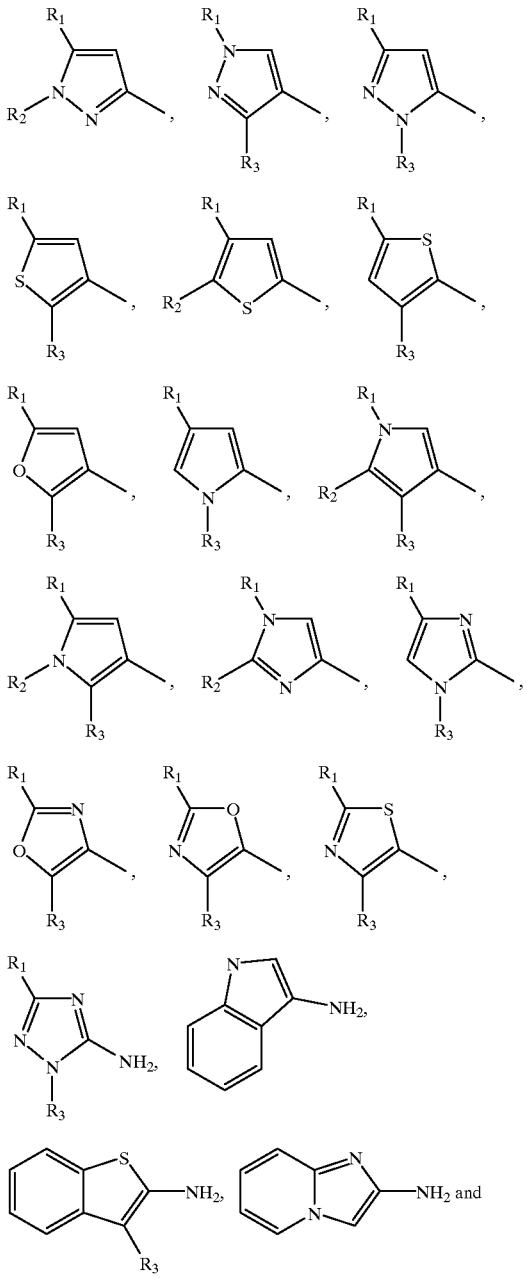

-continued

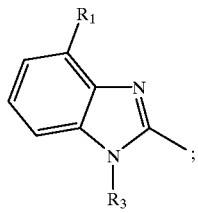

X is S, O or $NR_6$;

Y is N—H;

$R_1$ is selected from the group consisting of:
a) $C_{3-10}$ branched alkyl, which is optionally partially or fully halogenated, and optionally substituted with one to three phenyl, naphthyl or heteroaryl groups (each such heteroaryl group being independently selected from pyridinyl and thienyl), each such phenyl, naphthyl or heteroaryl group being substituted with 0 to 5 groups selected from halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, amninocarbonyl and di($C_{1-3}$) alkylaminocarbonyl;
b) a cycloalkyl group selected from cyclopropyl, cyclobutyl, cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups, or an analog of such cycloalkyl group wherein instead of one to three ring methylene groups there are groups independently selected from O, S, CHOH, >C=O, >C=S and NH;
c) $C_{3-10}$ branched alkenyl which is optionally partially or fully halogenated, and which is optionally substituted with one to three groups independently selected from $C_{1-5}$ branched or unbranched alkyl, phenyl, naphthyl or heteroaryl, with each such heteroaryl group being independently selected from pyridinyl and thienyl and each such phenyl, naphthyl or heteroaryl group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, cyano, $C_{1-3}$ alkyloxy which is optionally partially or fully halogenated, aminocarbonyl and mono- or di($C_{1-3}$)alkylaminocarbonyl;
d) a cycloalkenyl group selected from cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;
e) an alkoxy carbonyl group selected from methoxycarbonyl, ethoxycarbonyl and propoxycarbonyl;

$R_2$ is selected from the group consisting of the following, when B is a carbon atom or an amino nitrogen: hydrogen, $C_{1-6}$ branched or unbranched alkyl which is optionally partially or fully halogenated, benzoyl and phenylsulfonyl;

$R_3$ is selected from the group consisting of the following, when D is a carbon atom or an amino nitrogen:
a) phenyl, naphthyl and heteroaryl (wherein said heteroaryl group is selected from pyridinyl, pyrimidinyl, pyrazinyl, pyridazinyl, pyrrolyl, imidazolyl, pyrazolyl, thienyl, furyl, isoxazolyl, isothiazolyl, quinolinyl, isoquinolinyl, indolyl, benzimidazolyl, benzofuranyl and benzoxazolyl), wherein such phenyl, naphthyl or heteroaryl group is optionally substituted with one to three groups independently selected from $C_{1-6}$ branched or unbranched alkyl, phenyl, naphthyl, heteroaryl selected from the group set forth immediately above, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, hydroxy, cyano, $C_{1-3}$ alkyloxy which is optionally partially or fully halogenated, phenyloxy, naphthyloxy, hetararyloxy wherein the heteroaryl moiety is selected from the group set forth above in this subparagraph, nitro, amino, mono- or di-($C_{1-3}$)alkylamino, phenylamino, naphthylamino, heteroarylamino wherein the heteroaryl moiety is selected from the group set forth above in this subparagraph, aminocarbonyl, a mono- or di-($C_{1-3}$)alkyl aminocarbonyl, $C_{1-4}$ branched or unbranched alkyl oxycarbonyl, $C_{1-5}$ alkylcarbonyl $C_{1-4}$ branched or unbranched alkyl, amino $C_{1-5}$ alkyl, mono- or di-($C_{1-3}$)alkylamino($C_{1-5}$)alkyl, aminosulfonyl, di-($C_{1-3}$) alkylaminosulfonyl;
b) fused aryl (selected from benzocyclobutanyl, indanyl, indenyl, dihydronaphthyl, tetrahydronaphthyl, benzocycloheptanyl and benzocycloheptenyl), and fused heteroaryl (selected from cyclopentenopyridine, cyclohexanopyridine, cyclopentanothiophene and cyclohexanothiophene), wherein the fused aryl or fused heteroaryl ring is substituted with 0 to 3 groups independently selected from phenyl, naphthyl and heteroaryl (wherein each such heteroaryl is selected from pyridinyl and thienyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heteroaryloxy (wherein the heteroaryl moiety is selected from the group set forth above in this subparagraph), amino, mono- or di-($C_{1-3}$)alkylamino, phenylamino, naphthylamino, heteroarylamino (wherein the heteroaryl moiety is selected from the group set forth above in this subparagraph), aminocarbonyl, a mono- or di-($C_{1-3}$)alkyl aminocarbonyl, $C_{1-4}$ branched or unbranched alkyl oxycarbonyl, $C_{1-5}$ alkylcarbonyl $C_{1-4}$ branched or unbranched alkyl, amino $C_{1-5}$ alkyl, mono- or di-($C_{1-3}$)alkylamino($C_{1-5}$)alkyl, aminosulfonyl, di-($C_{1-3}$)alkylaminosulfonyl;
c) a cycloalkyl group selected from cyclopentanyl, cyclohexanyl and cycloheptanyl, which cycloalkyl group is optionally partially or fully halogenated and which is optionally substituted with one to three $C_{1-3}$ alkyl groups;
d) a cycloalkenyl group selected from cyclopentenyl, cyclohexenyl and cycloheptenyl, wherein such cycloalkenyl group is optionally substituted with one to three $C_{1-3}$ alkyl groups; and,
e) acetyl, benzoyl and phenylsulfonyl;

or $R_1$ and $R_2$ taken together may optionally form a fused phenyl or pyridinyl ring, $R_5$ is selected from the group consisting of:
a) phenyl, naphthyl and heteroaryl (wherein such heteroaryl is selected from pyridinyl, pyrimidinyl, pyrazinyl, pyridazinyl, pyrazolyl, thienyl, quinolinyl, isoquinolinyl, indolyl, benzimidazolyl, benzofuranyl, benzoxazolyl, benzisoxazolyl), wherein such phenyl, naphthyl or heteroaryl group optionally bears one to three groups selected from phenyl, naphthyl and heteroaryl (wherein each such heteroaryl moiety is independently selected from the group defined above in this subparagraph), $C_{1-6}$ branched or unbranched alkyl which is optionally partially or fully halogenated, cyclopropyl, cyclobutyl, cyclopentanyl, cyclohexanyl, halo, cyano, $C_{1-3}$ alkyloxy which is optionally partially or fully halogenated, phenyloxy, naphthyloxy, mono- or di-($C_{1-3}$) alkylamino, phenylamino, naphthylamino, mono- or di-($C_{1-3}$) alkylaminocarbonyl, amino($C_{1-5}$) alkyl or alkenyl, di-($C_{1-3}$)alkylamino($C_{1-5}$)alkyl or alkenyl, phenylamino($C_{1-3}$)alkyl or alkenyl, naphthylamino($C_{1-3}$)alkyl or alkenyl, phenylamido($C_{1-3}$)alkyl or alkenyl, naphthylamido($C_{1-3}$)alkyl or alkenyl, phenyl($C_{1-5}$)alkyl or alkenyl and naphthyl($C_{1-5}$)alkyl or alkenyl;

b) fused aryl (selected from benzocyclobutanyl, indanyl, indenyl, dihydronaphthyl, tetrahydronaphthyl, benzocycloheptanyl and benzocycloheptenyl), and fused heteroaryl (selected from cyclopentenopyridine, cyclohexanopyridine, cyclopentanothiophene and cyclohexanothiophene), wherein the fused aryl or fused heteroaryl ring bears 0 to 3 groups selected from phenyl, naphthyl, heteroaryl (wherein such heteroaryl is selected from pyridinyl and thienyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy, amino, mono- or di-($C_{1-3}$) alkylamino, phenylamino, naphthylamino, aminocarbonyl, mono- or di-($C_{1-3}$) alkylaminocarbonyl, amino($C_{1-5}$)alkyl or alkenyl, di-($C_{1-3}$)alkylamino($C_{1-5}$)alkyl or alkenyl, phenylamino($C_{1-3}$)alkyl or alkenyl, naphthylamino($C_{1-3}$)alkyl or alkenyl, phenylamido($C_{1-3}$)alkyl or alkenyl, naphthylamido($C_{1-3}$)alkyl or alkenyl, phenyl($C_{1-5}$) alkyl or alkenyl and naphthyl($C_{1-5}$)alkyl or alkenyl;

c) cycloalkyl selected from cyclopentanyl, cyclohexanyl and cycloheptanyl, which cycloalkyl group is optionally partially or fully halogenated and which is optionally substituted with one to three $C_{1-3}$ alkyl groups;

d) cycloalkenyl selected from cyclopentenyl and cyclohexenyl, which cycloalkenyl group is optionally partially or fully halogenated and which is optionally substituted with one to three $C_{1-3}$ alkyl groups; and e) phenyl($C_{1-5}$ branched or unbranched)alkyl, and naphthyl($C_{1-5}$ branched or unbranched)alkyl, wherein the phenyl or naphthyl ring is substituted with 0 to 5 groups selected from the group consisting of phenyl, naphthyl, heteroaryl (selected from pyridinyl and thienyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy or heteroaryloxy (wherein the heteroaryl moiety is as defined above in this subparagraph);

$R_6$ is hydrogen, cyano or $C_{1-6}$ branched or unbranched alkyl which is optionally partially or fully halogenated.

In a penultimately preferred generic aspect, the invention provides compounds of the above formula I, wherein:

the heterocyclic moiety

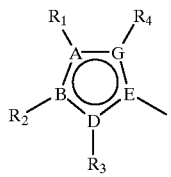

is selected from the group consisting of:

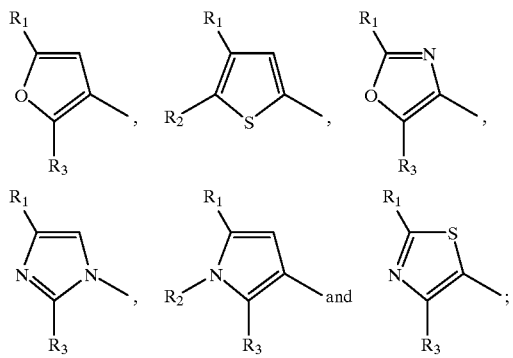

X is S or O;
Y is N—H;
$R_1$ is selected from the group consisting of:

a) $C_{3-10}$ branched alkyl, which is optionally partially or fully halogenated, and optionally substituted with one to three phenyl, naphthyl or heteroaryl groups (each such heteroaryl group being independently selected from pyridinyl and thienyl), each such phenyl, naphthyl or heteroaryl group being substituted with 0 to 3 groups selected from halogen, $C_{1-6}$ branched or unbranched alkyl which is optionally partially or fully halogenated, $C_{3-8}$ cycloalkyl, hydroxy, cyano and $C_{1-3}$ alkyloxy which is optionally partially or fully halogenated;

b) a cycloalkyl group selected from cyclopropyl, cyclobutyl, cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups, or an analog of such cycloalkyl group wherein instead of one to three ring methylene groups there are groups independently selected from O, S, CHOH, >C=O, >C=S and NH;

c) $C_{3-10}$ branched alkenyl which is optionally partially or fully halogenated, and which is optionally substituted with one to three groups independently selected from $C_{1-5}$ branched or unbranched alkyl, phenyl, naphthyl or heteroaryl, with each such heteroaryl group being independently selected from pyridinyl and thienyl and each such phenyl, naphthyl or heteroaryl group being substituted with 0 to 3 groups selected from halogen, $C_{1-6}$ branched or unbranched alkyl which is optionally partially or fully halogenated, cyclopropyl, cyclobutyl, cyclopentanyl, hydroxy, cyano, and $C_{1-3}$ alkyloxy which is optionally partially or fully halogenated;

d) a cycloalkenyl group selected from cyclopentenyl, cyclohexenyl, bicyclohexenyl and bicycloheptenyl, wherein such cycloalkenyl group is optionally substituted with one to three $C_{1-3}$ alkyl groups;

e) an alkoxy carbonyl group selected from methoxycarbonyl, ethoxycarbonyl and propoxycarbonyl;

$R_2$ is selected from the group consisting of the following, when B is a carbon atom or an amino nitrogen: hydrogen, $C_{1-6}$ branched or unbranched alkyl which is optionally partially or fully halogenated, acetyl, benzoyl and phenylsulfonyl;

$R_3$ is selected from the group consisting of the following, when D is a carbon atom or an amino nitrogen:

a) phenyl, naphthyl and heteroaryl (wherein said heteroaryl group is selected from pyridinyl, quinolinyl and isoquinolinyl), wherein such phenyl, naphthyl or heteroaryl group is optionally substituted with one to three groups independently selected from $C_{1-6}$ branched or unbranched alkyl, phenyl, naphthyl, heteroaryl selected from the group set forth immediately above, $C_{1-4}$ branched or unbranched alkyl which is optionally partially or fully halogenated, cyclopropyl, cyclobutyl, cyclopentanyl, cyclohexanyl, phenyl $C_{1-5}$ alkyl, halo, hydroxy, cyano, $C_{1-3}$ alkyloxy which is optionally partially or fully halogenated, phenyloxy, naphthyloxy, heteraryloxy wherein the heteroaryl moiety is selected from the group set forth above in this subparagraph, mono- or di-$(C_{1-3})$alkylamino, phenylamino, naphthylamino, heteroarylamino wherein the heteroaryl moiety is selected from the group set forth above in this subparagraph, aminocarbonyl, a mono- or di-$(C_{1-3})$alkyl aminocarbonyl, $C_{1-5}$ alkylcarbonyl $C_{1-4}$ branched or unbranched alkyl, amino $C_{1-5}$ alkyl and mono- or di-$(C_{1-3})$alkylamino$(C_{1-5})$alkyl;

b) fused aryl (selected from benzocyclobutanyl, indanyl, indenyl, dihydronaphthyl and tetrahydronaphthyl), and fused heteroaryl (selected from cyclopentenopyridine, cyclohexanopyridine, cyclopentanothiophene and cyclohexanothiophene), wherein the fused aryl or fused heteroaryl ring is substituted with 0 to 3 groups independently selected from phenyl, naphthyl and heteroaryl (wherein each such heteroaryl is selected from pyridinyl and thienyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heteroaryloxy (wherein the heteroaryl moiety is selected from the group set forth above in this subparagraph), mono- or di-$(C_{1-3})$alkylamino, phenylamino, naphthylamino, heteroarylamino (wherein the heteroaryl moiety is selected from the group set forth above in this subparagraph), aminocarbonyl, a mono- or di-$(C_{1-3})$alkyl aminocarbonyl, amino $C_{1-5}$ alkyl and mono- or di-$(C_{1-3})$alkylamino$(C_{1-5})$alkyl;

c) a cycloalkyl group selected from cyclopentanyl, cyclohexanyl and cycloheptanyl, which cycloalkyl group is optionally partially or fully halogenated and which is optionally substituted with one to three $C_{1-3}$ alkyl groups;

d) a cycloalkenyl group selected from cyclopentenyl, cyclohexenyl and cycloheptenyl, wherein such cycloalkenyl group is optionally substituted with one to three $C_{1-3}$ alkyl groups;

e) acetyl, benzoyl and phenylsulfonyl; and, or $R_1$ and $R_2$ taken together may optionally form a fused phenyl or pyridinyl ring, $R_5$ is selected from the group consisting of:

a) phenyl, naphthyl and heteroaryl (wherein such heteroaryl is selected from pyridinyl, thienyl, quinolinyl, isoquinolinyl and indolyl), wherein such phenyl, naphthyl or heteroaryl group optionally bears one to three groups selected from phenyl, naphthyl and heteroaryl (wherein each such heteroaryl moiety is independently selected from the group defined above in this subparagraph), $C_{1-6}$ branched or unbranched alkyl which is optionally partially or fully halogenated, cyclopropyl, cyclobutyl, cyclopentanyl, cyclohexanyl, halo, cyano, $C_{1-3}$ alkyloxy which is optionally partially or fully halogenated, phenyloxy, naphthyloxy, phenylamino, naphthylamino phenylamino$(C_{1-3})$alkyl or alkenyl, naphthylamino$(C_{1-3})$alkyl or alkenyl, phenylamido$(C_{1-3})$alkyl or alkenyl, naphthylamido$(C_{1-3})$alkyl or alkenyl, heteroarylamido$(C_{1-3})$alkyl or alkenyl (wherein the heteroaryl moiety is as defined above in this subparagraph);

b) fused aryl (selected from benzocyclobutanyl, indanyl, indenyl, dihydronaphthyl, tetrahydronaphthyl, benzocycloheptanyl and benzocycloheptenyl), and fused heteroaryl (selected from cyclopentenopyridine, cyclohexanopyridine, cyclopentanothiophene and cyclohexanothiophene), wherein the fused aryl or fused heteroaryl ring bears 0 to 3 groups selected from phenyl, naphthyl, heteroaryl (wherein such heteroaryl is selected from pyridinyl and thienyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy, , phenylamino, naphthylamino, phenylamino$(C_{1-3})$alkyl or alkenyl, naphthylamino$(C_{1-3})$alkyl or alkenyl, phenylamido$(C_{1-3})$alkyl or alkenyl, naphthylamido$(C_{1-3})$alkyl or alkenyl, heteroarylamido $(C_{1-3})$alkyl or alkenyl (wherein the heteroaryl moiety is as defined above in this subparagraph); and, c) phenyl$(C_{1-5}$ branched or unbranched)alkyl, and naphthyl$(C_{1-5}$ branched or unbranched)alkyl, wherein the phenyl or naphthyl ring is substituted with 0 to 3 groups selected from the group consisting of phenyl, naphthyl, heteroaryl (selected from pyridinyl and thienyl), $C_{1-6}$ branched or unbranched alkyl which is optionally partially or fully halogenated, halo, cyano, $C_{1-3}$ alkyloxy which is optionally partially or fully halogenated, phenyloxy, naphthyloxy or heteroaryloxy (wherein the heteroaryl moiety is as defined above in this subparagraph).

In an ultimately preferred generic aspect, the invention provides compounds of the formula I, wherein:

the heterocyclic moiety

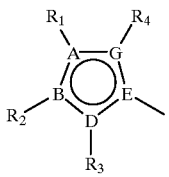

is selected from the group consisting of:

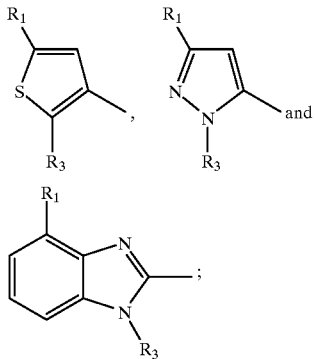

X is S or O;
Y is N—H;
$R_1$ is selected from the group consisting of:
a) $C_{3-7}$ branched alkyl, which is optionally partially or fully halogenated, and optionally substituted with one to three phenyl or heteroaryl groups (each such heteroaryl group being independently selected from pyridinyl and thienyl), each such phenyl or heteroaryl group being substituted with 0 to 3 groups selected from halogen, $C_{1-6}$ branched or unbranched alkyl which is optionally partially or fully halogenated, $C_{3-8}$ cycloalkyl and $C_{1-3}$ alkyloxy which is optionally partially or fully halogenated;
b) a cycloalkyl group selected from cyclopropyl, cyclobutyl, cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups;
c) $C_{3-7}$ branched alkenyl which is optionally partially or fully halogenated, and which is optionally substituted with one to three groups independently selected from $C_{1-5}$ branched or unbranched alkyl, phenyl or heteroaryl, with each such heteroaryl group being independently selected from pyridinyl and thienyl and each such phenyl or heteroaryl group being substituted with 0 to 3 groups selected from halogen, $C_{1-6}$ branched or unbranched alkyl which is optionally partially or fully halogenated, cyclopropyl, cyclobutyl, cyclopentanyl and $C_{1-3}$ alkyloxy which is optionally partially or fully halogenated;
$R_3$ is selected from the group consisting of the following, when D is a carbon atom or an amino nitrogen:
a) phenyl, naphthyl and heteroaryl (wherein said heteroaryl group is selected from pyridinyl, quinolinyl and isoquinolinyl), wherein such phenyl, naphthyl or heteroaryl group is optionally substituted with one to three groups independently selected from $C_{1-6}$ branched or unbranched alkyl, phenyl, naphthyl, heteroaryl selected from the group set forth immediately above, $C_{1-6}$ branched or unbranched alkyl which is optionally partially or fully halogenated, cyclopropyl, cyclobutyl, cyclopentanyl, cyclohexanyl, halo, hydroxy, cyano, $C_{1-3}$ alkyloxy which is optionally partially or fully halogenated, phenyloxy, hetaryloxy wherein the heteroaryl moiety is selected from the group set forth above in this subparagraph, mono- or di-($C_{1-3}$) alkylamino, phenylamino, heteroarylamino wherein the heteroaryl moiety is selected from the group set forth above in this subparagraph, aminocarbonyl, a mono- or di-($C_{1-3}$)alkyl aminocarbonyl and mono- or di-($C_{1-3}$)alkylamino($C_{1-5}$)alkyl;
b) fused aryl (selected from benzocyclobutanyl, indanyl, indenyl, dihydronaphthyl and tetrahydronaphthyl), and fused heteroaryl (selected from cyclopentenopyridine, cyclohexanopyridine, cyclopentanothiophene and cyclohexanothiophene), wherein the fused aryl or fused heteroaryl ring is substituted with 0 to 3 groups independently selected from phenyl and heteroaryl (wherein each such heteroaryl is selected from pyridinyl and thienyl), $C_{1-6}$ branched or unbranched alkyl which is optionally partially or fully halogenated, halo, cyano, $C_{1-3}$ alkyloxy which is optionally partially or fully halogenated, phenyloxy, heteroaryloxy (wherein the heteroaryl moiety is selected from the group set forth above in this subparagraph), mono- or di-($C_{1-3}$) alkylamino, phenylamino, heteroarylamino (wherein the heteroaryl moiety is selected from the group set forth above in this subparagraph), aminocarbonyl, a mono- or di-($C_{1-3}$)alkyl aminocarbonyl and mono- or di-($C_{1-3}$)alkylamino($C_{1-5}$)alkyl;
c) a cycloalkyl group selected from cyclopentanyl, cyclohexanyl and cycloheptanyl, which cycloalkyl group is optionally partially or fully halogenated and which is optionally substituted with one to three $C_{1-3}$ alkyl groups;
d) acetyl, benzoyl and phenylsulfonyl; and,
$R_5$ is selected from the group consisting of:
a) phenyl, naphthyl and heteroaryl (wherein such heteroaryl is selected from pyridinyl, thienyl, quinolinyl and isoquinolinyl), wherein such phenyl, naphthyl or heteroaryl group optionally bears one to three groups selected from phenyl and heteroaryl (wherein each such heteroaryl moiety is independently selected from the group defined above in this subparagraph), $C_{1-6}$ branched or unbranched alkyl which is optionally partially or fully halogenated, cyclopropyl, cyclobutyl, cyclopentanyl, cyclohexanyl, halo, cyano, $C_{1-3}$ alkyloxy which is optionally partially or fully halogenated, phenyloxy, phenylamino;
b) fused aryl (selected from benzocyclobutanyl, indanyl, indenyl, dihydronaphthyl, tetrahydronaphthyl, benzocycloheptanyl and benzocycloheptenyl), and fused heteroaryl (selected from cyclopentenopyridine, cyclohexanopyridine, cyclopentanothiophene and cyclohexanothiophene), wherein the fused aryl or fused heteroaryl ring bears 0 to 3 groups selected from phenyl, $C_{1-6}$ branched or unbranched alkyl which is optionally partially or fully halogenated, halo, cyano, $C_{1-3}$ alkyloxy which is optionally partially or fully halogenated, phenyloxy and phenylamino; and,
c) phenyl($C_{1-5}$ branched or unbranched)alkyl, and naphthyl($C_{1-5}$ branched or unbranched)alkyl, wherein the phenyl or naphthyl ring is substituted with 0 to 3 groups selected from the group consisting of phenyl, $C_{1-6}$ branched or unbranched alkyl which is optionally partially or fully halogenated, halo, cyano, $C_{1-3}$ alkyloxy which is optionally partially or fully halogenated and phenyloxy.

Specifically preferred compounds in accordance with the invention are those selected from the group consisting of:

1-[5-tert-Butyl-2-(2-methylpyridin-5-yl)-2H-pyrazol-3-yl]-3-(4-chlorophenyl)urea;

1-(5-tert-Butyl-2-p-tolyl-2H-pyrazol-3-yl)-3-(4-methoxynaphthalen-1-yl)urea;

1-(5-tert-Butyl-2-(3,4-dimethylphenyl)-2H-pyrazol-3-yl)-3-(4-fluorophenyl)urea;

1-(5-tert-Butyl-2-p-tolyl-2H-pyrazol-3-yl)-3-(2-fluorophenyl)urea; and

1-[5-tert-Butyl-2-(pyridin-3-yl)-2H-pyrazol-3-yl]-3-(4-cyanonaphthalen-1-yl)urea.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula I can exist in more than one tautomeric form. The invention includes all such tautomers.

The invention includes pharmaceutically acceptable derivatives of compounds of formula I. A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of the invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene- 2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N-($C_1$–$C_4$ alkyl)$_4^+$ salts.

In addition, the invention include prodrugs of the compounds of compounds of the formula I. Prodrugs include those compounds that, upon simple chemical transformation, are modified to produce a compound of formula I. Simple chemical transformations include hydrolysis, oxidation and reduction. Specifically, when a prodrug of this invention is administered to a patient, the prodrug may be transformed into a compound of formula I, thereby imparting the desired pharmacological effect.

GENERAL SYNTHETIC METHODS

The compounds of the invention may be prepared by Method A or B as illustrated in Scheme I.

Scheme I

Method A

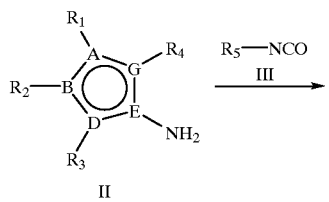

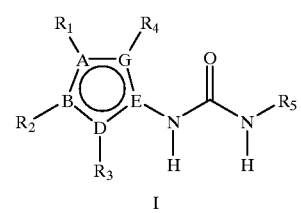

Method B

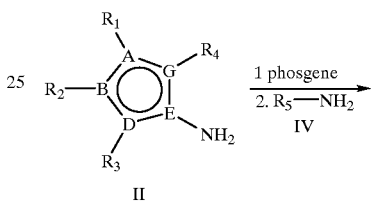

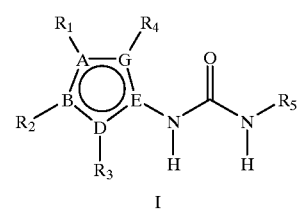

In Method A, a mixture of an aminoheterocycle of formula II and an arylisocyanate of formula III is dissolved in a non-protic, anhydrous solvent such as THF, ether, toluene, dioxane or ethyl acetate. The preferred solvent is THF. The mixture is stirred at between 0–45° C., preferably at 25° C., for 2–24 hr, and the volatiles are removed. Purification of the residue by recrystallization or silica gel chromatography, using hexanes and ethyl acetate as eluents, provides the product of formula I.

In Method B, an aminoheterocycle of formula II is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as $MgSO_4$ or $Na_2SO_4$, and the volatiles removed to provide the corresponding isocyanate of formula II. The isocyanate and arylamine IV are mixed in a non-protic, anhydrous solvent such as THF, ether, toluene, dioxane, methylene chloride or ethyl acetate. The preferred solvent is THF. The mixture is stirred at between 0–45° C., preferably at 25° C., for 2–24 hr, and the volatiles are removed. Purification of the residue by recrystallization or silica gel chromatography, using hexanes and ethyl acetate as eluents, provides the product of formula I.

The method used to produce an aminoheterocycle of formula II will depend on the nature of the desired heterocycle. In general, intermediates of formula II can be made by methods known to those skilled in the art. Some general methods are illustrated in the schemes below. Amines and isocyanates bearing R₅ used in Method A or B respectively are available commercially or easily prepared by methods known to those skilled in the art.

Desired aminopyrazoles of formula XII can be prepared as described in Scheme II. A hydrazine of formula VII, bearing substituent R₃, may be prepared by Method C or D. In Method C, an aryl bromide of formula V is dissolved in a non-protic, inert solvent, such as THF, 1,4-dioxane or diethyl ether, and cooled to low temperature under an inert atmosphere. The preferred temperature for the solution is −77° C. A strong base dissolved in a non-protic, inert solvent, such as hexanes, THF or ether, is added dropwise while maintaining a reaction temperature below 0° C. and preferably below −60° C. The preferred bases are alkyl lithium reagents and the most preferred is sec-butyl lithium. After the addition of the base, the reaction mixture is stirred for a period of time between thirty and ninety minutes or until all the starting aryl bromide has been consumed. An excess of dialkyl azodicarboxylate is added while maintaining a reaction temperature below 0° C. and preferably below −60° C. The preferred dialkyl azodicarboxylate is di-tert-butyl azodicarboxylate. The reaction is stirred at cold temperatures and warmed to room temperature after 0.5 hr to 2 hr. The reaction is quenched with the addition of water and the product extracted into a non-protic solvent, such as ethyl acetate, diethyl ether or chloroform. The organic layers are dried with agents such as MgSO₄ or Na₂SO₄ and the volatiles removed. The residue is dissolved in protic solvents, such as methanol or iso-propanol, cooled, preferably to 0–5° C. and treated with acid. Preferred acids are hydrochloric, hydrobromic, sulfuric and trifluoroacetic. The most preferred is hydrochloric in gaseous form. After the addition of excess acid the mixture is heated at the reflux temperature of the solvent until all starting material has been consumed. After cooling the product aryl-hydrazine of formula VII salt is filtered and dried.

Scheme II

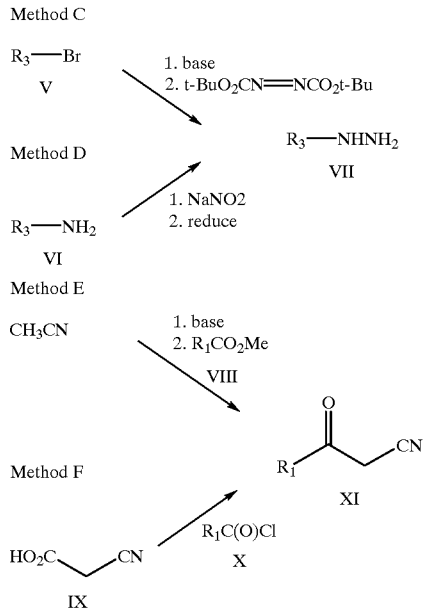

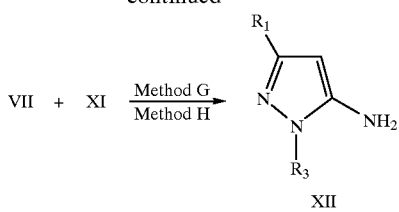

In Method D, an aryl amine bearing R₃ of formula VI is dissloved in a concentrated aqueous acid such as hydrochloric, hydrobromic and sulfuric and cooled to ice bath temperatures. The most preferred acid is hydrochloric with concentrations between 3–8N with the most preferred concentration of 6N. A nitrosating reagent in water is added dropwise while maintaining a cold temperature. The preferred temperature is 0–5° C. The preferred reagent is sodium nitrite. The reaction is stirred between 10–90 min and a reducing agent is added while maintaining cold temperatures. The preferred temperature is 0–5° C. Reducing agents include zinc, iron, samarium iodide and tin(II) chlroride. The most preferred agent is tin(II) chlroride dissolved in aqueous hydrochloride with a concentration of 3–8 N with a most preferred concentration of 6N. The reaction is stirred between 0.5–3 hr and quenched with alkali to a pH between 12–14. Alkali reagents include sodium hydroxide, potassium hydroxide, lithium hydroxide and calcium hydroxide. The most preferred alkali reagent is potassium hydroxide. The aqueous solution is extracted with a non-protic organic solvent, such as diethyl ether, chloroform, ethyl acetate and methylene chloride. The organic layers are dried with agents such as MgSO₄ and Na₂SO₄ and the volatiles removed to provide the aryl-hydrazine (VII) which can be carried forward without further purification.

A β-ketonitrile bearing R₁ (XI) may be prepared by Method E or F. In Method E, a metal hydride, such as sodium hydride, potassium hydride or lithium hydride, is suspended in an anhydrous, inert, non-protic solvent, such as diethyl ether, THF and dioxane, at temperatures between 35–85° C. The most preferred metal hydride is sodium hydride and the most preferred solvent is THF at a temperature of 75° C. An alkyl ester, preferably a methyl ester (VIII), and acetonitrile is dissolved in an anhydrous, inert, non-protic solvent, such as diethyl ether, THF or dioxane and added dropwise to the metal hydride suspension. The preferred solvent is THF. The mixture is kept at elevated temperatures between 3–24 hours, cooled to room temperature and diluted with a non-protic solvent and aqueous acid. The organic layer is washed with water and brine, dried, with agents such as MgSO₄ and Na₂SO₄, and the volatiles removed to provide the β-ketonitrile (XI) which could be used without further purification.

Alternatively, following Method F, a solution of a strong base, such as alkyl lithium reagents and metal amide reagents, such as n-butyl lithium, sec-butyl lithium, methyl lithium and lithium diisopropylamide, in an anhydrous, inert, non-protic solvent, such as diethyl ether, THF and dioxane, is cooled below 0° C. The preferred base is n-butyl lithium, the preferred solvent is THF and the preferred temperature is −77° C. A solution of cyanoacetic acid (IX) in an anhydrous, inert, non-protic solvent, such as diethyl ether, THF and dioxane, and most preferrably THF, is added dropwise while maintaining a reaction temperature below 0° C. and preferably at −77° C. The reaction is stirred between 10–45 min while warming to 0° C. The solution of the dianion of cyanoacetic is cooled to temperatures below −25° C. and preferably at −77° C. An alkyl acid chloride (X) dissolved in an anhydrous, inert, non-protic solvent, such as diethyl ether, THF and dioxane, and most preferrably THF, is added. The reaction mixture is warmed to 0° C. between 10–30 min. and quenched with aqueous acid. The product is extracted with an organic solvent, such as chloroform, ethyl acetate, ether and methylene chloride. The combined organic extracts are dried, with agents such as $MgSO_4$ and $Na_2SO_4$, and the volatiles removed to provide the β-ketonitrile (XI) which could be used without further purification.

The desired aminopyrazole (XII) may then be prepared by Method G or H. I Method G, aryl hydrazine VII and β-ketonitrile XI are mixed in an organic solvent, such as toluene, ethanol, iso-propanol or t-butanol. The preferred solvent is ethanol. An acid, such as hydrochloric acid, p-toluene sulfonic acid, sulfuric acid, is added, The preferred acid is concentrated hydrochloric acid. The mixture is heated to temperatures between 50–100° C., preferably at 80° C., for 10–24 hr and cooled to room. The mixture is diluted with non-protic organic solvent, such as ethyl acetate, ether, chloroform and methylene chloride, and washed with aqueous alkali, such as sodium bicarbonate and potassium carbonate. The organic layer is dried, with agents such as $MgSO_4$ and $Na_2SO_4$, and the volatiles removed to provide a residue which is purified by recrystallization or silica gel chromatography using hexanes and ethyl acetate as eluents. The product-rich fractions are collected and the volatiles removed to provide the desired amonopyrazole (XII).

Alternatively, using Method H, aryl hydrazine VII and β-ketonitrile XI are mixed in an organic solvent, such as toluene, ethanol, iso-propanol and t-butanol. The preferred solvent is toluene. The mixture is heated at reflux temperatures for 3–24 hrs with azeotropic removal of water and worked up as described above providing the aminopyrazole XII.

A general synthesis for desired aminothiophenes is illustrated in Scheme III, Method I.

Scheme III

Method I

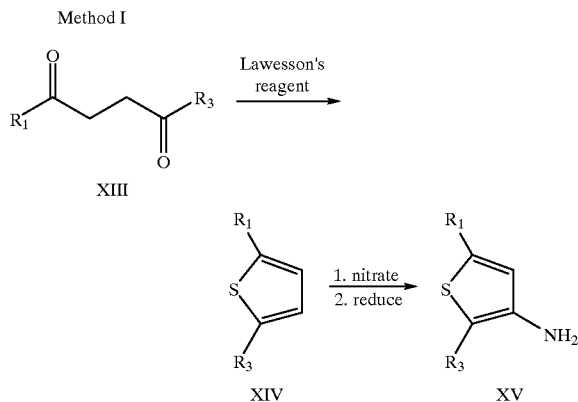

A mixture of 1-aryl-5-alkyl-butane-1,4-dione (XIII) and a sulfating reagent, such as Lawesson's reagent and phosphorous (V) sulfide, and preferably Lawesson's reagent, is dissolved in a non-protic, anhydrous solvent, such as toluene, THF and dioxane. The preferred solvent is toluene. The mixture is heated at elevated temperatures and preferably at a solvent-refluxing temperature for 1–10 hr. The volatiles are removed and the residue is purified by silica gel chromatography using hexanes and ethyl acetate as eluent. The product-rich fractions are collected and the volatiles removed to provide the substituted thiophene XIV.

A mixture of substituted thiophene XIV is dissolved in a solvent such as acetic anhydride or acetic acid. The preferred solvent is acetic anhydride. The mixture is cooled to 0–30° C. and preferably to −10° C. A solution of concentrated nitric acid in a solvent such as acetic anhydride or acetic acid, with the preferred solvent being acetic anhydride and cooled to 0–30° C. and preferably to −10° C. is added. The mixture is stirred between 10–120 min, poured onto ice and extracted with a non-protic solvent such as diethyl ether, chloroform, ethyl acetate or methylene chloride. The organic extracts are washed with aqueous alkali, dried with agents such as $MgSO_4$ and $Na_2SO_4$ and the volatiles removed. The residue is purified by silica gel chromatography using hexanes and ethyl acetate as eluents. The product-rich fractions are collected and the volatiles removed to provide the 2-aryl-5-alkyl-3-nitrothiophene. The 2-aryl-5-alkyl-3-nitrothiophene is reduced by metals, such as iron, tin and zinc or catalytic hydrogenation. The preferred reduction occurs with iron in acetic acid at temperatures between 5–110° C. and preferably at 100° C. for 5–30 min. After cooling to room temperature the reaction is diluted with water, neutralized with alkali, such as sodium hydroxide, potassium hydroxide, potassium carbonate or sodium bicarbonate, and extracted with a non-protic solvent such as diethyl ether, ethyl acetate or methylene chloride. The organic extracts are dried with agents such as $MgSO_4$ and $Na_2SO_4$ and the volatiles removed to provide the desired aminothiophene XV.

Other desired aminoheterocycles can be prepared by methods known in the art and described in the literature. The examples that follow are illustrative and, as recognized by one skilled in the art, particular reagents or conditions could be modified as needed for individual compounds. Intermediates used in the schemes below are either commercially available or easily prepared from commercially available materials by those skilled in the art.

Scheme IV outlines a general scheme for desired aminofurans as described by Stevenson et al. (J. Am. Chem. Soc., 1937, 59, 2525). An ethyl aroylacetate (XVI) is dissolved in a non-protic solvent, such as ether or THF, and treated with a strong base, such as sodium, sodium ethoxide or sodium hydride, and the anion is reacted with a bromomethyl alkylketone (XVII) at low temperatures, such as 0° C. After stirring the reaction until no starting material remains, it is poured onto cold water and extracted with a non-protic solvent. The combined extracts are dried with agents such as $MgSO_4$ or $Na_2SO_4$. The diketo-ester (XVIII) may be carried forward without further purification or purified by distillation or silica gel chromatography. The diketo-ester in a protic solvent, such as ethanol, is heated in the presence of a mineral acid, such as sulfuric and hydrochloric, for 5–10 hr. and extracted with a non-protic solvent. The combined extracts are dried with agents such as $MgSO_4$ or $Na_2SO_4$. The furan-ester (XIX) may be carried forward without further purification or purified by distillation or silica gel chromatography. The furan-ester in a protic solvent, such as ethanol, is treated with hydrazine hydrate and the mixture heated for 2–5 days. The hydrazide is isloated as above and treated with hot formic acid and the resulting furan-amine (XX) purified by distillation or silica gel chromatography.

Scheme IV

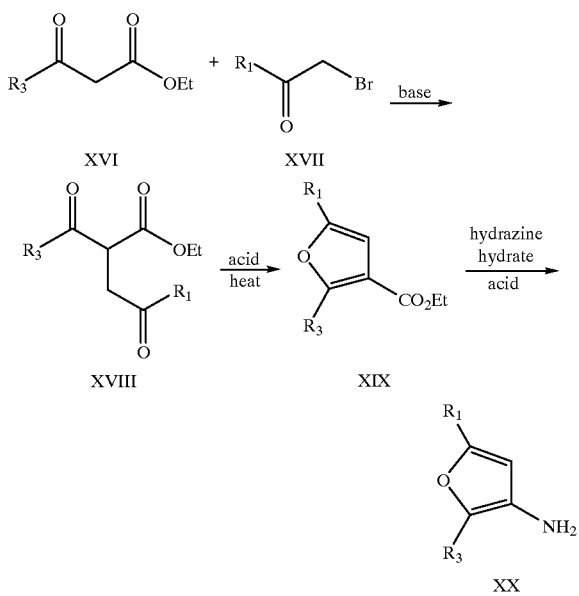

The synthesis of substituted 4-aminooxazoles may be achieved analogous to a procedure described by Lakhan et al. (J. Het. Chem., 1988, 25, 1413) and illustrated in Scheme V. A mixture of aroyl cyanide (XXI), aldeyde (XXII) and anhydrous ammonium acetate in acetic acid is heated at 100–110° C. for 3–6 hr, cooled to room temperature and quenched with water. Extraction by a non-protic solvent provides the product XXIII which can be carried forward without further purification or purified by recrystallization or silica gel chromatography.

Scheme V

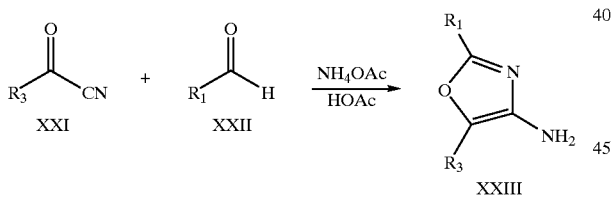

The synthesis of substituted 3-aminopyrroles (XXVII) may be achieved in a manner analogous to Aiello et al., J. Chem. Soc. Perkins Trans. I, 1981, 1. This is outlined in Scheme VI. A mixture of aryldioxoalkane (XXIV) and amine (XXV) in acetic acid is heated at 100–110° C. for 3–6 hr and worked up in the usual manner. The product (XXVI) in acetic acid is treated with a nitrating agent, such as nitric acid and potassium nitrate in concentrated sulfuric acid. The mixture is poured onto cold water and extracted with a non-protic solvent. The combined extracts are dried with agents such as $MgSO_4$ and $Na_2SO_4$. Removal of the volatiles provides the nitro-pyrrole which which may be carried forward without further purification or purified by recrystallization or silica gel chromatography. The nitro-pyrrole is reduced to the amine with iron in acetic acid or by catalytic hydrogenation using palladium on activated carbon. The aminopyrrole (XXVII) may be carried forward without further purification or purified by recrystallization or silica gel chromatography.

Scheme VI

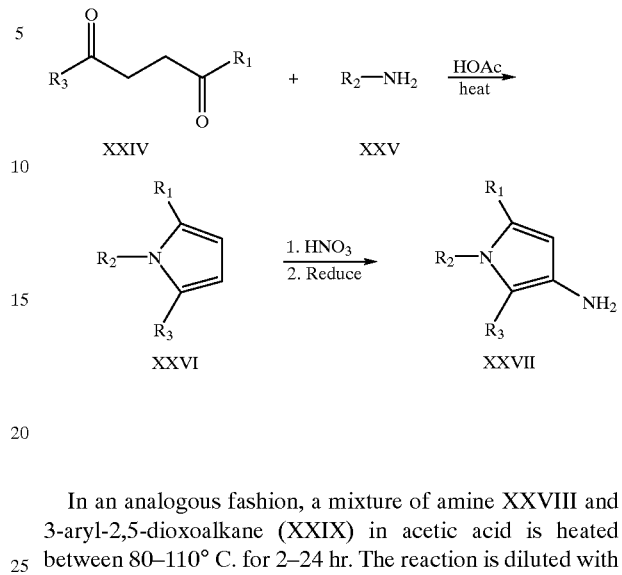

In an analogous fashion, a mixture of amine XXVIII and 3-aryl-2,5-dioxoalkane (XXIX) in acetic acid is heated between 80–110° C. for 2–24 hr. The reaction is diluted with water and extracted with an organic solvent. The combined extracts are dried with agents such as $MgSO_4$ or $Na_2SO_4$ and the volatiles removed. The resulting pyrrole is treated with a nitrating agent and subsequently reduced to XXX as described above. The product may be carried forward without further purification or purified by recrystallization or silica gel chromatography. This process is illustrated in Scheme VII.

Scheme VII

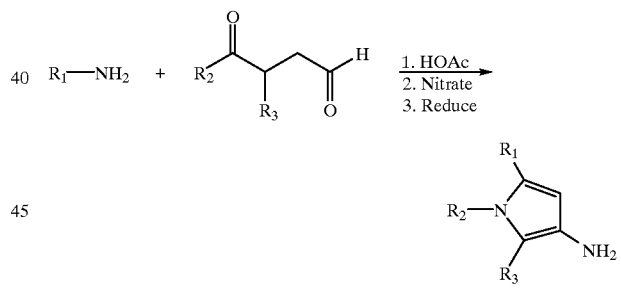

Substituted 5-aminothiazoles (XXXIV) may be prepared in a manner analogous to Gerwald et al., J. Prakt. Chem. 1973, 315, 539. As illustrated in Scheme VIII, to a mixture of aminocyanide XXXI, aldehyde XXXII and sulfur in an anhydrous solvent, such as ethanol and methanol, is added dropwise a base, such as triethylamine. The mixture is heated at 50° C. for 1–3 hr. The mixture is cooled and the excess sulfur removed. Acetic acid is added to neutralize the mixture and the solid collected. The imine XXXIII is treated with acid, such as hydrchloric and toluenesulfonic acid, in water and an organic solvent. After the staring material is consumed the reaction is worked up and the product XXXIV may be carried forward without further purification or purified by recrystallization or silica gel chromatography.

Scheme VIII

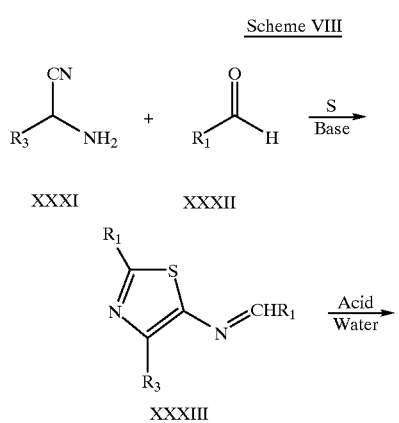

A synthesis of substituted 2-aminothiophenes (XXXVI), analogous to a procedure described by Gewald et al. (J. Prakt. Chem., 1973, 315, 539) is illustrated in Scheme IX. A mixture of disubstituted thiophene-3-carboxylic acid (XXXV) in a protic solvent, such as acetic acid, at a temperature of 0–50° C. is treated with a nitrating agent, such as nitric acid or potassium nitrate in concentrated sulfuric acid. After the starting material has been consumed the reaction is poured onto ice and the product extracted with a non-protic solvent. The combined extracts are dried with agents such as $MgSO_4$ and $Na_2SO_4$ and the volatiles removed. The nitrothiophene is reduced to the amine with iron in acetic acid or by catalytic hydrogenation using palladium on activated carbon. The amino-thiophene may be carried forward without further purification or purified by recrystallization or silica gel chromatography.

Scheme IX

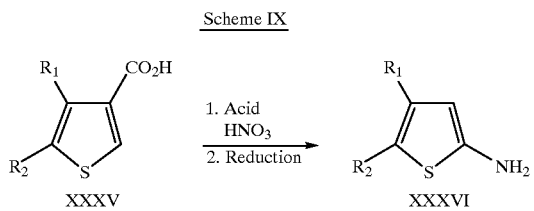

1,5-Disubstituted-3-aminopyrazoles (XXXIX) may be prepared as shown in Scheme X, in a fashion analogous to the procedure described by Ege et al. (J. Het. Chem., 1982, 19, 1267). Potassium is added to anhydrous t-butanol and the mixture cooled to 5° C. Hydrazine XXXVII is added, followed by cyanodibromoalkane XXXVIII. The mixture is heated at refluxing temperatures for 3–10 hr. The mixture is cooled to room temperature and poured onto ice water. The product is extracted with an organic solvent. The combined extracts are dried with agents such as $MgSO_4$ or $Na_2SO_4$ and the volatiles removed. The product XXXIX may be carried forward without further purification or purified by recrystallization or silica gel chromatography.

Scheme X

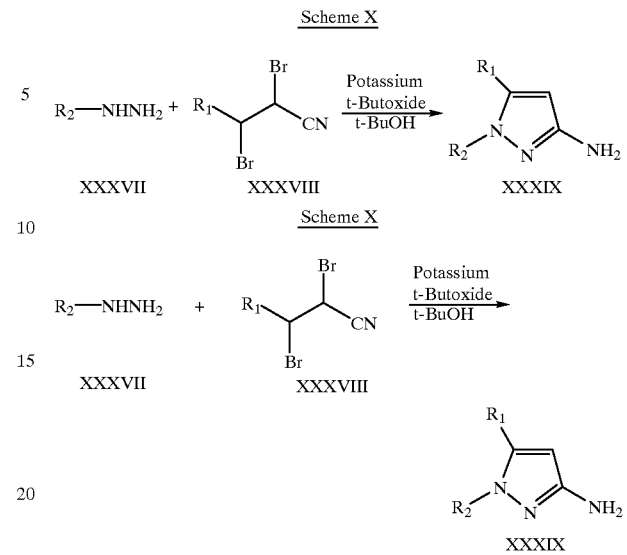

The synthesis of 2-amino-3,5-disubstituted thiophenes shown in Scheme XI, is done in a fashion analogous to Knoll et al., J. Prakt. Chem., 1985, 327, 463. A mixture of substituted N-(3-aminothioacryloyl)-formamidine (XL) and substituted bromide (XLI) in a protic solvent, such as methanol or ethanol, is heated, preferably at a reflux temperature, for 5–30 min and cooled below room temperature. The product thiopheneimine is filtered and dried. The thiophene-imine XLII is converted to the thiopheneamine (XLIII) by treatment with aqueous acid.

Scheme XI

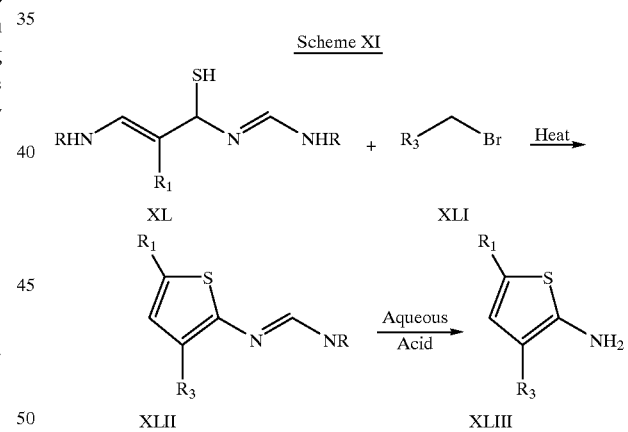

The synthesis of 1,4-disubstituted-2-aminopyrroles (XLVII) may be accomplished in a manner analogous to Brodrick et al. (J. Chem. Soc. Perkin Trans. I, 1975, 1910), and as illustrated in Scheme XII. The potassium salt of formylnitrile XLIV in water is treated with amine XLV and acetic acid and the mixture heated at 50–90° C. for 5–30 min. The aminonitrile XLVI is collected by filtration upon cooling and then is stirred at room temperature with a base such as ethanolic potassium ethoxide for 2–5 hr and the volatiles removed. The residue is diluted with water and extracted with an organic solvent. The combined extracts are dried with agents such as $MgSO_4$ and $Na_2SO_4$ and the volatiles removed. The product (XLVII) may be carried forward without further purification or purified by recrystallization or silica gel chromatography.

Scheme XII

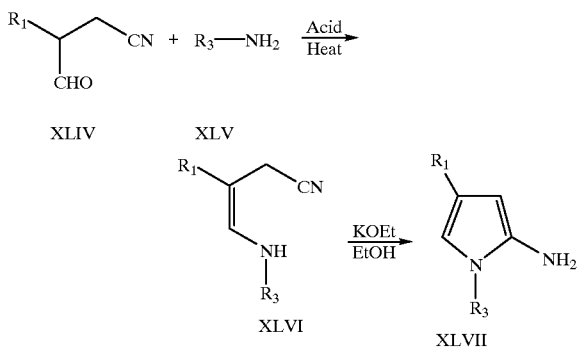

The preparation of 1,2-disubstituted-4-aminoimidazoles by reduction of the corresponding nitro compound, for example with iron in acetic acid or catalytic hydrogenation may be accomplished as described by Al-Shaar et al. (J. Chem. Soc. Perkin Trans. I, 1992, 2779) and illustrated in Scheme XIII.

Scheme XII

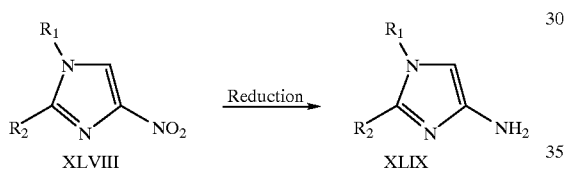

2,4-Disubstituted 5-aminooxazoles (LIV) may be prepared in a manner analogous to the procedure described by Poupaert et al. (Synthesis, 1972, 622) and illustrated in Scheme XIV. Acid chloride L is added to a cold mixture of 2-aminonitrile LI and a base such as triethylamine in a non-protic solvent, such as THF, benzene, toluene or ether. The preferred temperature is 0° C. The mixture is stirred for 12–24 hr and washed with water. The volatiles are removed and the product LII treated with ethylmercaptan and dry hydrogen chloride in dry methylene chloride for 5–30 min. The solid 5-imino-1,3-oxazole hydrochloride (LIII) is collected by filtration, dissolved in dry pyridine and the solution saturated with hydrogen sulfide during 4 hr at 0° C. The mixture is diluted with an organic solvent and washed with water and dried. Removal of the volatiles provides the 5-amino-1,3-oxazole product (LIV) which may be carried forward without further purification or be purified by silica gel chromatography.

Scheme XIV

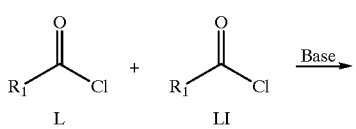

-continued

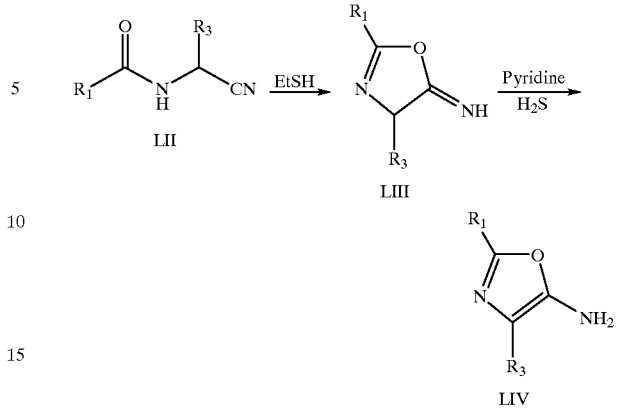

The synthesis of 1,4-disubstituted-2-aminopyrazoles may be accomplished as illustrated in Scheme XV and described in Lancini et al., J. Het. Chem., 1966, 3, 152. To a mixture of substituted aminoketone (LV) and cyanamide in water and acetic acid was added aqueous sodium hydroxide until pH 4.5 is reached. The mixture is heated at 50–90° C. for 1–5 hr, cooled and basicified with ammonium hydroxide. The product LVI is collected by filtration and dried.

Scheme XV

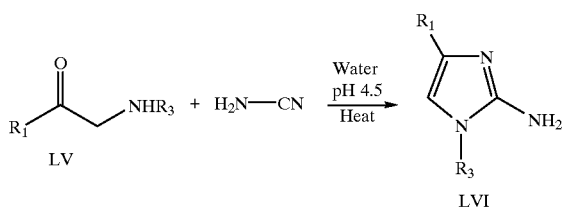

Scheme XV

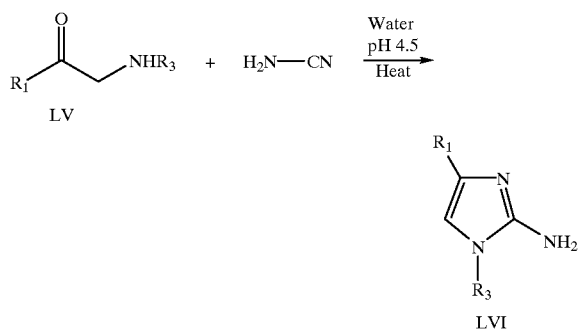

As in the cases described above, the synthesis of many other aminoheterocycles useful as intermediates may be accomplished by methods similar to those described in the literature or known to those skilled in the art. Several additional examples are illustrated in Scheme XVI. 2,5-Disubstituted-3-aminotriazoles (LVII) have been described by Plenkiewicz et al. (Bull. Chem. Soc. Belg. 1987, 96, 675). 1,3-Disubstituted-4-aminopyrazoles (LVIII) have been described by Guarneri et al. (Gazz. Chim. Ital. 1968, 98, 569). Damany et al. (Tetrahedron, 1976, 32, 2421) describe a 2-amino-3-substituted benzothiophene (LIX). A 3-aminoindole (LX) is described by Foresti et al. (Gazz. Chim. Ital., 1975, 125, 151). Bristow et al. (J. Chem. Soc., 1954, 616) describe an imidazo[1,2-a]pyridin-2-yl amine (LXI).

Scheme XVI

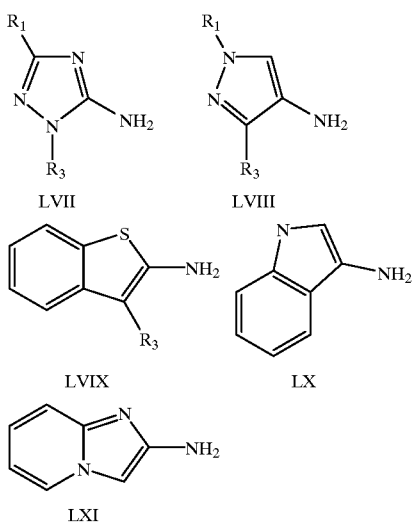

METHODS OF THERAPEUTIC USE

The compounds of the invention effectively block inflammatory cytokine production from cells. The inhibition of cytokine production is an attractive means for preventing and treating a variety of disorders associated with excess cytokine production, e.g., diseases and pathological conditions involving inflammation. Thus, the compounds of the invention are useful for the treatment of such conditions. These encompass chronic inflammatory diseases including, but not limited to, rheumatoid arthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat other disorders associated with the activity of elevated levels of proinflammatory cytokines such as responses to various infectious agents and a number of diseases of autoimmunity such as toxic shock syndrome, osteoarthritis, diabetes and inflammatory bowel diseases unrelated to those listed above are discussed above, in the Background of the Invention.

For therapeutic use, the compounds of the invention may be administered in any conventional dosage form in any conventional manner. Routes of administration include, but are not limited to, intravenously, intramuscularly, subcutaneously, intrasynovially, by infuision, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of formula (I) (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

SYNTHETIC EXAMPLES

Example 1

Synthesis of 1-(5-tert-butyl-2-phenylthiophen-3-yl)-3-(4-chlorophenyl)urea

Synthetic Scheme I

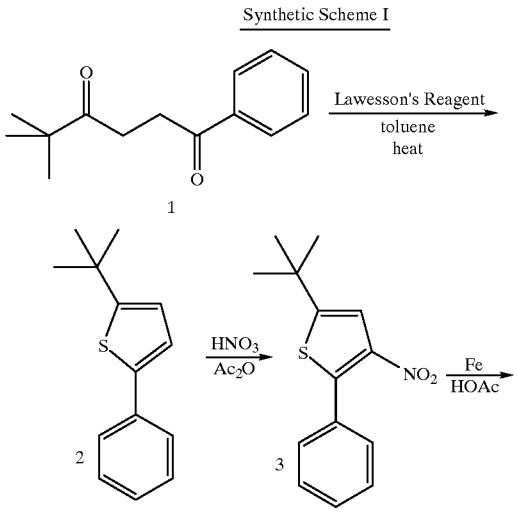

-continued

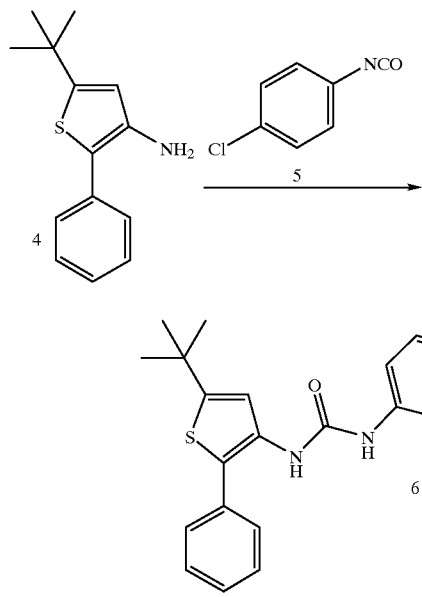

A mixture of 1-phenyl, 5,5-dimethylhexane-1,5-dione (1, 1.18 gm) and Lawesson's reagent (2.62 gm) in 25 mL toluene was heated at reflux for 2 hours, cooled to room temperature and most of the volatiles were removed under a stream of nitrogen. The residue was purified by flash chromatography using 50% ether in hexanes as the eluent. Concentration in vacuo of the product-rich fractions provided thiophene 2. To 2 (0.81 gm) in 5 mL acetic anhydride at −10° C. was added a cold (−10° C.) solution of nitric acid (0.24 mL, d=1.49) in 2 mL acetic anhydride. The mixture was stirred 45 minutes, poured onto ice and extracted with ether. The combined organic extracts were washed with water, saturated NaHCO$_3$, brine and dried (MgSO$_4$) and the volatiles removed in vacuo. Purification of the residue with flash chromatography using 5% ethyl acetate in hexanes as the eluent provided nitrothiophene 3. A mixture of 3 (0.67 gm) and iron powder (1.4 gm) in 10 mL acetic acid was heated at 100° C. for 10 minutes, cooled to room temperature, diluted with water, basicified with solid potassium carbonate and extracted with ethyl acetate. The combined extracts were washed with brine and dried (MgSO$_4$). Removal of the volatiles in vacuo provided aminothiophene 4. A mixture of 4 (0.13 gm) and 4-chlorophenyl isocyanate (5, 82 mg) in 2 mL anhydrous THF was stirred at room temperature overnight and the volatiles removed in vacuo. Purification of the residue by flash chromatography using 11% ethyl acetate in hexanes as the eluent and concentration of the product rich-fraction in vacuo provided urea 6.

Example 2

Synthesis of 1-(5-tert-butyl-2-phenyl-2H-pyrazol-3-yl)-3-(indan-2-yl)urea

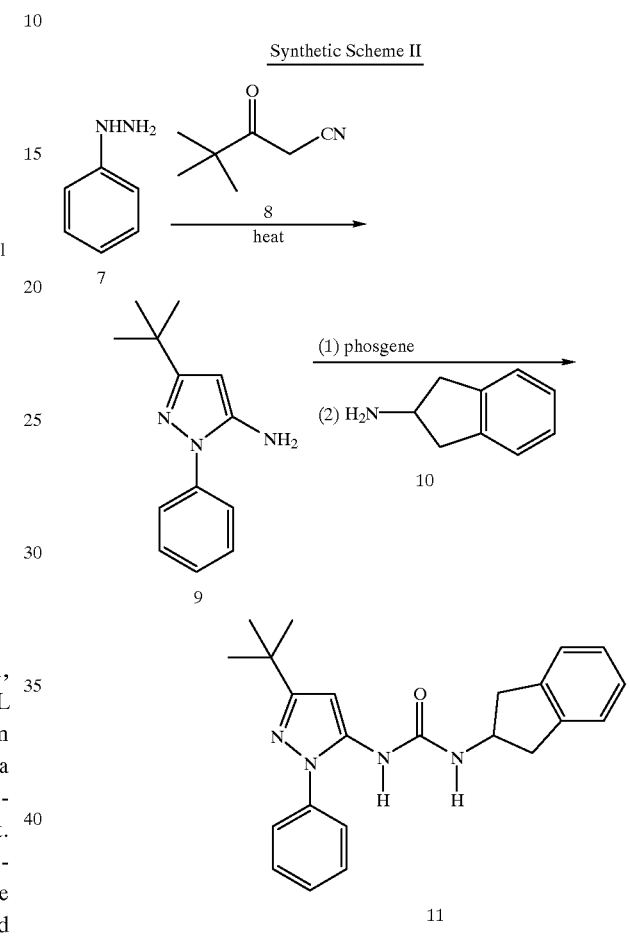

A solution of phenylhydrazine (7, 10.9 gm) and 4,4-dimethyl-3-oxopentanenitrile (8, 10.2 gm) in 25 mL of toluene was heated at reflux with azeotropic removal of water. After 4 hours the volatiles were removed in vacuo and the residue purified by flash silica gel chromatography using 17% ethyl acetate in hexanes as the eluent. Concentration in vacuo of the product-rich fractions provided pyrazole 9. A mixture of 9 (0.52 gm) and phosgene (2.5 mL of a 1.9 M toluene solution) in 25 mL methylene chloride and 25 mL of aqueous saturated sodium bicarbonate was vigorously stirred for 10 minutes in an ice bath and the aqueous layer extracted with methylene chloride. The combined organic layers were dried (magnesium sulfate) and the volatiles removed in vacuo. A mixture of the isocyanate (195 mg) and 2-aminoindan (10, 142 mg) in 5 mL methylene chloride was stirred at room temperature overnight. Removal of the volatiles in vacuo provide a residue which was crystallized with ethyl acetate and hexanes and furnished urea 11 as a white solid.

Example 3
Synthesis of 1-(1-phenyl-1H-benzoimidazol-2-yl)-3-(4-chlorophenyl)urea

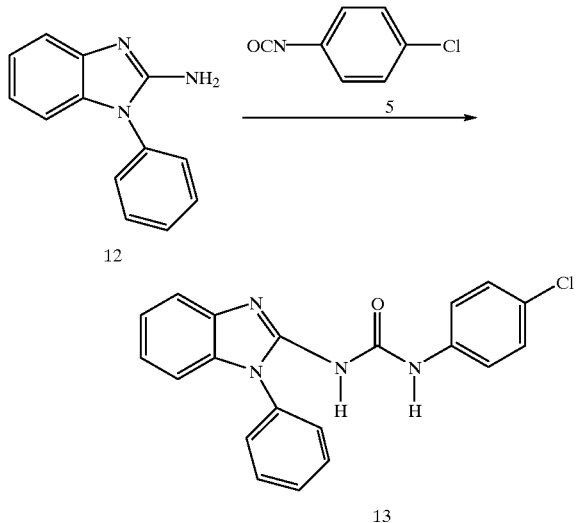

A mixture of 2-amino-1-phenylbenzimidazole (12) and 4-chlorophenyl isocyanate (5) was stirred at room temperature in methylene chloride overnight. Removal of the volatiles in vacuo provide a residue which was purified by recrystallization in ethyl acetate and hexanes to afford urea 13.

Using methods analogous to those described above, the compounds of the invention described in the following Table 1 were either prepared (those compounds for which melting points are given) or could be prepared (those compounds for which no melting points are given).

TABLE 1

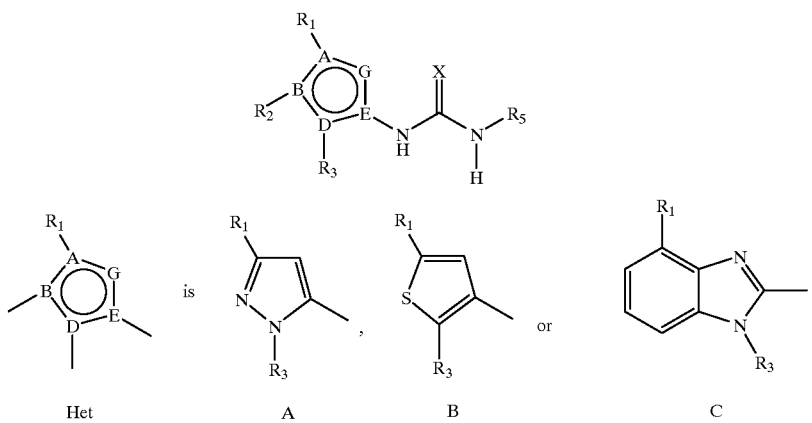

| Ex. No. | Het | $R_1$ | $R_3$ | $R_5$ | X | m.p. °C. |
|---|---|---|---|---|---|---|
| 4 | A | t-butyl | 4-methylphenyl | 2,4-dichlorophenyl | O | 230.5–231 |
| 5 | A | 1-methylcyclohexan-1-yl | 2-methylpyridin-5-yl | 5-fluoroindan-1-yl | O | |
| 6 | A | 1,1-dimethylprop-1-yl | 4-methylphenyl | phenyl | O | |
| 7 | A | 1-methyl-1-chloromethylethyl | 4-methylphenyl | phenyl | O | |
| 8 | A | t-butyl | 4-methylphenyl | 1-naphthyl | O | 198–199 |
| 9 | A | t-butyl | 4-methylphenyl | 2-pyridinyl | O | |
| 10 | A | t-butyl | 4-methylphenyl | benzyl | S | |
| 11 | A | t-butyl | 4-$CF_3$-phenyl | 1,2,3,4-tetrahydronaphth-2-yl | O | |
| 12 | A | cyclopentanyl | 4-methylphenyl | 4-cyanonaphth-1-yl | O | |
| 13 | A | t-butyl | 3-fluoro-phenyl | 5-iso-quinolinyl | O | |
| 14 | A | t-butyl | 4-methylphenyl | phenyl | O | 179–180 |
| 15 | A | t-butyl | 4-methylphenyl | 2-fluoro-phenyl | O | 103–104 |
| 16 | A | t-butyl | 4-methylphenyl | 2-chloro-phenyl | O | 197.5–198 |
| 17 | A | t-butyl | 4-methylphenyl | 4-cyano-2-ethylphenyl | O | 180–181 |
| 18 | A | t-butyl | 4-methylphenyl | 4-methoxyphenyl | O | 209–210 |
| 19 | A | t-butyl | 4-methylphenyl | 3-methoxynaphth-1-yl | O | 117–118 |
| 20 | A | t-butyl | 4-methylphenyl | 4-phenyl-napth-1-yl | O | 110–120 |
| 21 | A | t-butyl | 4-methylphenyl | 4-cyanonapth-1-yl | O | 252–255 |

TABLE 1-continued

| Ex. No. | Het | R₁ | R₃ | R₅ | X | m.p. °C. |
|---|---|---|---|---|---|---|
| 22 | A | t-butyl | 4-methylphenyl | 4-chloronapth-1-yl | O | 194–195 |
| 23 | A | t-butyl | methyl | 4-chloronapth-1-yl | O | 230–231 |
| 24 | A | t-butyl | phenyl | 1,2,3,4-tetrahydronapth-1-yl | O | 212–213 |
| 25 | A | t-butyl | phenyl | 1-naphthyl | O | 107 |
| 26 | A | t-butyl | phenyl | 3,4-methylenedioxyphenyl | O | 221 |
| 27 | A | t-butyl | phenyl | 5-indanyl | O | 192 |
| 28 | A | t-butyl | phenyl | 2-chloro-4-cyano-phenyl | O | 131–132 |
| 29 | A | t-butyl | 3-bromo-phenyl | 4-fluoro-phenyl | O | 210–211 |
| 30 | A | t-butyl | 4-cyanophenyl | 2-chloro-phenyl | O | 184–185 |
| 31 | A | t-butyl | 4-CF₃-phenyl | 2-fluoro-phenyl | O | 196–197 |
| 32 | A | t-butyl | 3,4-dimethylphenyl | 4-fluoro-phenyl | O | 223–225 |
| 33 | A | t-butyl | 3-chloro-4-methylphenyl | phenyl | O | 175 |
| 34 | A | t-butyl | 3-nitrophenyl | phenyl | O | 177–178 |
| 34 | A | t-butyl | 3-dimethylaminophenyl | phenyl | O | 184–185 |
| 35 | A | t-butyl | 4-pyridinyl | phenyl | O | 178–180 |
| 36 | A | t-butyl | 3-pyridinyl | 4-cyclopentylnapth-1-yl | O | 204–206 |
| 37 | A | t-butyl | 2-methylpyridin-5-yl | 2-fluoro-phenyl | O | 108–110 |
| 38 | A | 1-methylcyclohexan-1-yl | phenyl | phenyl | O | 86–88 |
| 39 | A | 1-methylcyclopropyl-1-yl | phenyl | phenyl | O | 161 |
| 40 | A | 1,1-dimethyl-2-chloroethyl | phenyl | phenyl | O | 191–192 |
| 41 | A | 1,1-dimethylpropyl | phenyl | phenyl | O | 175 |
| 42 | A | 1-methyltetrahydropyran-4-yl | phenyl | 2-chloro-phenyl | O | 84–86 |
| 43 | A | t-butyl | phenyl | 4-chloro-phenyl | S | 164–166 |
| 44 | B | t-butyl | phenyl | 4-chloro-phenyl | O | 199–200 |
| 45 | B | t-butyl | phenyl | 2-indanyl | O | |
| 46 | B | 1-methylcyclopent-1-yl | Pyridin-3-yl | 1-naphthyl | O | |
| 47 | C | hydrogen | phenyl | 2,4-dichloro-phenyl | O | |
| 48 | C | methyl | phenyl | 2-indanyl | O | |
| 49 | C | hydrogen | phenyl | 4-chloro-phenyl | O | 143–144 |

ASSESSMENT OF BIOLOGICAL PROPERTIES

Inhibition of TNFα Production in THP Cells

The inhibition of TNFα production can be measured in lipopolysaccharide stimulated THP cells. All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). The assay was performed under sterile conditions; only test compound preparation was nonsterile. Initial stock solutions were made in DMSO followed by dilution into RPMI 1640 2-fold higher than the desired final assay concentration. Confluent THP.1 cells (2×10⁶ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% CO₂ prior to stimulation with lipopolysaccharide (LPS; 1 μg/ml final; Sigma L-2630, from E.coli serotype 0111.B4; stored as 1 mg/ml stock in endotoxin screened distilled H₂O at −80° C.). Blanks (unstimulated) received H₂O vehicle; final incubation volume was 250 μl. Overnight incubation (18–24 hr) proceeded as described above. The assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated IC50 value is the concentration of the test compound that caused a 50% decrease in TNFα production.

Representative compounds listed in the above Synthetic Examples were evaluated and all had IC₅₀<10 μM in this assay.

Inhibition of Other Cytokines

By similar methods using peripheral blood monocytic cells, appropriate stimuli, and commercially available ELISA kits for a particular cytokine, inhibition of IL-1β, GM-CSF, IL-6 and IL-8 was demonstrated by representatives from Table 1.

What is claimed is:

1. A compound of the formula I

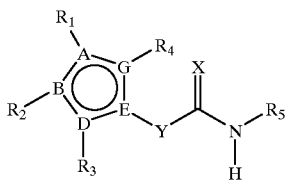

(I)

wherein:

the heterocyclic moiety

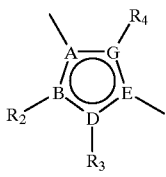

is selected from the group consisting of:

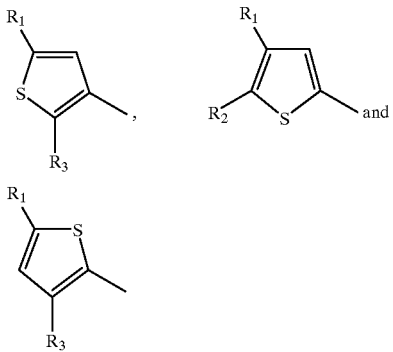

X is S, O or $NR_6$;

Y is $CHR_7$ or N—H;

$R_1$ is selected from the group consisting of:

(a) $C_{3-10}$ branched alkyl, which is optionally partially or fully halogenated, and optionally substituted with one to three phenyl, naphthyl or heteroaryl independently selected from pyridinyl, pyrimidinyl, pyrazinyl, pyridazinyl, pyrrolyl, imidazolyl, pyrazolyl, thienyl, furyl, isoxazolyl and isothiazolyl, each phenyl, naphthyl or heteroaryl group being substituted with 0 to 5 groups selected from halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, aminocarbonyl and di($C_{1-3}$)alkylaminocarbonyl;

(b) a cycloalkyl group selected from cyclopropyl, cyclobutyl, cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups, or an analog of said cycloalkyl group wherein instead of one to three ring methylene groups there are groups independently selected from O, S, CHOH, >C=O, >C=S and NH;

(c) $C_{3-10}$ branched alkenyl which is optionally partially or fully halogenated, and which is optionally substituted with one to three groups independently selected from $C_{1-5}$ branched or unbranched alkyl, phenyl, naphthyl or heteroaryl independently selected from pyridinyl, pyrimidinyl, pyrazinyl, pyridazinyl, pyrrolyl, imidazolyl, pyrazolyl, thienyl, furyl, isoxazolyl and isothiazolyl, and each phenyl, naphthyl or heteroaryl group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, cyano, $C_{1-3}$ alkyloxy which is optionally partially or fully halogenated, aminocarbonyl and mono- or di($C_{1-3}$)alkylaminocarbonyl;

(d) a cycloalkenyl group selected from cyclopentenyl, cyclohexenyl, cyclohexadienyl, cycloheptenyl, cycloheptadienyl, bicyclohexenyl and bicycloheptenyl, wherein said cycloalkenyl group is optionally substituted with one to three $C_{1-3}$ alkyl groups;

(e) cyano; and, (f) an alkoxy carbonyl group selected from methoxycarbonyl, ethoxycarbonyl and propoxycarbonyl;

$R_2$ is selected from the group consisting of hydrogen, $C_{1-6}$ branched or unbranched alkyl which is optionally partially or fully halogenated, acetyl, benzoyl and phenylsulfonyl;

$R_3$ is selected from the group consisting of:

a) phenyl, naphthyl and heteroaryl selected from pyridinyl, pyrimidinyl, pyrazinyl, pyridazinyl, pyrrolyl, imidazolyl, pyrazolyl, thienyl, furyl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pteridinyl, phthalazinyl, naphthypyridinyl, quinoxalinyl, quinazolinyl, purinyl and indazolyl, wherein each phenyl, naphthyl or heteroaryl group is optionally substituted with one to five groups independently selected from $C_{1-6}$ branched or unbranched alkyl, phenyl, naphthyl, heteroaryl selected from the group set forth immediately above, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, hydroxy, cyano, $C_{1-3}$ alkyloxy which is optionally partially or fully halogenated, phenyloxy, naphthyloxy, hetaryloxy wherein the heteroaryl moiety is selected from the group set forth above in this subparagraph, nitro, amino, mono- or di-($C_{1-3}$)alkylamino, phenylamino, naphthylamino, heteroarylamino wherein the heteroaryl moiety is selected from the group set forth above in this subparagraph, aminocarbonyl, a mono- or di-($C_{1-3}$)alkyl aminocarbonyl, $C_{1-4}$ branched or unbranched alkyl oxycarbonyl, $C_{1-5}$ alkylcarbonyl $C_{1-4}$ branched or unbranched alkyl, amino $C_{1-5}$ alkyl, mono- or di-($C_{1-3}$)alkylamino($C_{1-5}$)alkyl, aminosulfonyl, di-($C_{1-3}$)alkylaminosulfonyl;

b) fused aryl selected from benzocyclobutanyl, indanyl, indenyl, dihydronaphthyl, tetrahydronaphthyl, benzocycloheptanyl and benzocycloheptenyl, and fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene, wherein the fused aryl or fused heteroaryl ring is substituted with 0 to 3 groups independently selected from phenyl, naphthyl and heteroaryl selected from pyridinyl, pyrimidinyl, pyrazinyl, pyridazinyl, pyrrolyl, imidazolyl, pyrazolyl, thienyl, furyl, isoxazolyl and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heteroaryloxy wherein the heteroaryl moiety is selected from the group set forth above in this subparagraph, nitro, amino, mono- or di-$(C_{1-3})$ alkylamino, phenylamino, naphthylamino, heteroarylamino wherein the heteroaryl moiety is selected from the group set forth above in this subparagraph, aminocarbonyl, a mono- or di-$(C_{1-3})$alkyl aminocarbonyl, $C_{1-4}$ branched or unbranched alkyl oxycarbonyl, $C_{1-5}$ alkylcarbonyl $C_{1-4}$ branched or unbranched alkyl, amino $C_{1-5}$ alkyl, mono- or di-$(C_{1-3})$alkylamino$(C_{1-5})$alkyl, aminosulfonyl, di-$(C_{1-3})$alkylaminosulfonyl;

c) a cycloalkyl group selected from cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups;

d) a cycloalkenyl group selected from cyclopentenyl, cyclohexenyl, cyclohexadienyl, cycloheptenyl, cycloheptadienyl, bicyclohexenyl and bicycloheptenyl, wherein said cycloalkenyl group is optionally substituted with one to three $C_{1-3}$ alkyl groups; and, e) acetyl, benzoyl and phenylsulfonyl;

or $R_1$ and $R_2$ taken together optionally form a fused phenyl ring;

$R_5$ is selected from the group consisting of:

a) phenyl, naphthyl and heteroaryl selected from pyridinyl, pyrimidinyl, pyrazinyl, pyridazinyl, pyrrolyl, imidazolyl, pyrazolyl, thienyl, furyl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl, wherein each phenyl, naphthyl or heteroaryl group optionally bears one to five groups selected from phenyl, naphthyl and heteroaryl wherein each heteroaryl moiety is independently selected from the group defined above in this subparagraph, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, halo, cyano, $C_{1-3}$ alkyloxy which is optionally partially or fully halogenated, phenyloxy, naphthyloxy, nitro, amino, mono- or di-$(C_{1-3})$ alkylamino, phenylamino, naphthylamino, aminocarbonyl, mono- or di-$(C_{1-3})$ alkylaminocarbonyl, amino$(C_{1-5})$alkyl or alkenyl, di-$(C_{1-3})$alkylamino$(C_{1-5})$alkyl or alkenyl, phenylamino$(C_{1-3})$alkyl or alkenyl, naphthylamino$(C_{1-3})$alkyl or alkenyl, phenylamido$(C_{1-3})$alkyl or alkenyl, naphthylamido$(C_{1-3})$alkyl or alkenyl, phenyl$(C_{1-5})$alkyl or alkenyl and naphthyl$(C_{1-5})$alkyl or alkenyl;

b) fused aryl selected from benzocyclobutanyl, indanyl, indenyl, dihydronaphthyl, tetrahydronaphthyl, benzocycloheptanyl and benzocycloheptenyl, and fused heteroaryl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene, wherein the fused aryl or fused heteroaryl ring bears 0 to 3 groups selected from phenyl, naphthyl, heteroaryl selected from pyridinyl, pyrimidinyl, pyrazinyl, pyridazinyl, pyrrolyl, imidazolyl, pyrazolyl, thienyl, furyl, isoxazolyl and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, nitro, amino, mono- or di-$(C_{1-3})$ alkylamino, phenylamino, naphthylamino, aminocarbonyl, mono- or di-$(C_{1-3})$ alkylaminocarbonyl, amino$(C_{1-5})$alkyl or alkenyl, di-$(C_{1-3})$alkylamino$(C_{1-5})$alkyl or alkenyl, phenylamino$(C_{1-3})$alkyl or alkenyl, naphthylamino$(C_{1-3})$alkyl or alkenyl, phenylarnido$(C_{1-3})$alkyl or alkenyl, naphthylamido$(C_{1-3})$alkyl or alkenyl, phenyl$(C_{1-5})$alkyl or alkenyl and naphthyl$(C_{1-5})$alkyl or alkenyl; and, c) cycloalkyl selected from cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups;

d) cycloalkenyl selected from cyclopentenyl, cyclohexenyl, cyclohexadienyl, cycloheptenyl, cycloheptadienyl, bicyclohexenyl and bicycloheptenyl, which cycloalkenyl group is optionally partially or fully halogenated and which is optionally substituted with one to three $C_{1-3}$ alkyl groups; and e) phenyl$(C_{1-5}$ branched or unbranched)alkyl, and naphthyl $(C_{1-5}$ branched or unbranched)alkyl, wherein the phenyl or naphthyl ring is substituted with 0 to 5 groups selected from the group consisting of phenyl, naphthyl, heteroaryl selected from pyridinyl, pyrimidinyl, pyrazinyl, pyridazinyl, pyrrolyl, imidazolyl, pyrazolyl, thienyl, furyl, isoxazolyl and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy or heteroaryloxy wherein the heteroaryl moiety is as defined above in this subparagraph;

$R_6$ is hydrogen, cyano or $C_{1-6}$ branched or unbranched alkyl which is optionally partially or fully halogenated; and, $R_7$ is hydrogen or $C_{1-6}$ branched or unbranched alkyl, which is optionally partially or fully halogenated;

or a tautomer or pharmaceutically acceptable salt thereof.

2. A compound of the formula I according to claim 1, wherein:

X is S, O or $NR_6$;

Y is N—H;

$R_1$ is selected from the group consisting of:

a) $C_{3-10}$ branched alkyl, which is optionally partially or fully halogenated, and optionally substituted with one to three phenyl, naphthyl or heteroaryl independently selected from pyridinyl and thienyl, each phenyl, naphthyl or heteroaryl being substituted with 0 to 5 groups selected from halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, aminocarbonyl and di($C_{1-3}$)alkylaminocarbonyl;

b) a cycloalkyl group selected from cyclopropyl, cyclobutyl, cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups, or an analog of said cycloalkyl group wherein instead of one to three ring methylene groups there are groups independently selected from O, S, CHOH, >C=O, >C=S and NH;

c) $C_{3-10}$ branched alkenyl which is optionally partially or fully halogenated, and which is optionally substituted with one to three groups independently selected from $C_{1-5}$ branched or unbranched alkyl, phenyl, naphthyl or heteroaryl independently selected from pyridinyl and thienyl and each phenyl, naphthyl or heteroaryl group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, cyano, $C_{1-3}$ alkyloxy which is optionally partially or fully halogenated, aminocarbonyl and mono- or di($C_{1-3}$)alkylaminocarbonyl;

d) a cycloalkenyl group selected from cyclopentenyl, cyclohexenyl, cyclohexadienyl, cycloheptenyl, cycloheptadienyl, bicyclohexenyl and bicycloheptenyl, wherein each cycloalkenyl group is optionally substituted with one to three $C_{1-3}$ alkyl groups;

e) an alkoxy carbonyl group selected from methoxycarbonyl, ethoxycarbonyl and propoxycarbonyl;

$R_2$ is selected from the group consisting of hydrogen, $C_{1-6}$ branched or unbranched alkyl which is optionally partially or fully halogenated, acetyl, benzoyl and phenylsulfonyl;

$R_3$ is selected from the group consisting of:
a) phenyl, naphthyl and heteroaryl selected from pyridinyl, pyrimidinyl, pyrazinyl, pyridazinyl, pyrrolyl, imidazolyl, pyrazolyl, thienyl, furyl, isoxazolyl, isothiazolyl, quinolinyl, isoquinolinyl, indolyl, benzimidazolyl, benzofuranyl and benzoxazolyl, wherein each phenyl, naphthyl or heteroaryl group is optionally substituted with one to three groups independently selected from $C_{1-6}$ branched or unbranched alkyl, phenyl, naphthyl, heteroaryl selected from the group set forth immediately above, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, hydroxy, cyano, $C_{1-3}$ alkyloxy which is optionally partially or fully halogenated, phenyloxy, naphthyloxy, hetaryloxy wherein the heteroaryl moiety is selected from the group set forth above in this subparagraph, nitro, amino, mono- or di-($C_{1-3}$)alkylamino, phenylamino, naphthylamino, heteroarylamino wherein the heteroaryl moiety is selected from the group set forth above in this subparagraph, aminocarbonyl, a mono- or di-($C_{1-3}$)alkyl aminocarbonyl, $C_{1-4}$ branched or unbranched alkyl oxycarbonyl, $C_{1-5}$ alkylcarbonyl $C_{1-4}$ branched or unbranched alkyl, amino $C_{1-5}$ alkyl, mono- or di-($C_{1-3}$)alkylamino($C_{1-5}$)alkyl, aminosulfonyl, di-($C_{1-3}$)alkylaminosulfonyl;

b) fused aryl selected from benzocyclobutanyl, indanyl, indenyl, dihydronaphthyl, tetrahydronaphthyl, benzocycloheptanyl and benzocycloheptenyl, and fused heteroaryl selected from cyclopentenopyridine, cyclohexanopyridine, cyclopentanothiophene and cyclohexanothiophene, wherein the fused aryl or fused heteroaryl ring is substituted with 0 to 3 groups independently selected from phenyl, naphthyl and heteroaryl selected from pyridinyl and thienyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heteroaryloxy wherein the heteroaryl moiety is selected from the group set forth above in this subparagraph, amino, mono- or di-($C_{1-3}$)alkylamino, phenylamino, naphthylamino, heteroarylamino wherein the heteroaryl moiety is selected from the group set forth above in this subparagraph, aminocarbonyl, a mono- or di-($C_{1-3}$)alkyl aminocarbonyl, $C_{1-4}$ branched or unbranched alkyl oxycarbonyl, $C_{1-5}$ alkylcarbonyl $C_{1-4}$ branched or unbranched alkyl, amino $C_{1-5}$ alkyl, mono- or di-($C_{1-3}$)alkylamino($C_{1-5}$)alkyl, aminosulfonyl, di-($C_{1-3}$)alkylaminosulfonyl;

c) a cycloalkyl group selected from cyclopentanyl, cyclohexanyl and cycloheptanyl, which cycloalkyl group is optionally partially or fully halogenated and which is optionally substituted with one to three $C_{1-3}$ alkyl groups;

d) a cycloalkenyl group selected from cyclopentenyl, cyclohexenyl and cycloheptenyl, wherein said cycloalkenyl group is optionally substituted with one to three $C_{1-3}$ alkyl groups; and, e) acetyl, benzoyl and phenylsulfonyl;

or $R_2$ and $R_3$ taken together optionally form a fused phenyl ring;

$R_5$ is selected from the group consisting of:
a) phenyl, naphthyl and heteroaryl selected from pyridinyl, pyrimidinyl, pyrazinyl, pyridazinyl, pyrazolyl, thienyl, quinolinyl, isoquinolinyl, indolyl, benzimidazolyl, benzofuranyl, benzoxazolyl, benzisoxazolyl, wherein each phenyl, naphthyl or heteroaryl group optionally bears one to three groups selected from phenyl, naphthyl and heteroaryl wherein each heteroaryl moiety is independently selected from the group defined above in this subparagraph, $C_{1-6}$ branched or unbranched alkyl which is optionally partially or fully halogenated, cyclopropyl, cyclobutyl, cyclopentanyl, cyclohexanyl, halo, cyano, $C_{1-3}$ alkyloxy which is optionally partially or fully halogenated, phenyloxy, naphthyloxy, mono- or di-($C_{1-3}$) alkylamino, phenylamino, naphthylamino, mono- or di-($C_{1-3}$) alkylaminocarbonyl, amino($C_{1-5}$)alkyl or alkenyl, di-($C_{1-3}$)alkylamino($C_{1-5}$)alkyl or alkenyl, phenylamino($C_{1-3}$)alkyl or alkenyl, naphthylamino ($C_{1-3}$)alkyl or alkenyl, phenylamido($C_{1-3}$)alkyl or alkenyl, naphthylamido($C_{1-3}$)alkyl or alkenyl, phenyl($C_{1-5}$)alkyl or alkenyl and naphthyl($C_{1-5}$)alkyl or alkenyl;
b) fused aryl selected from benzocyclobutanyl, indanyl, indenyl, dihydronaphthyl, tetrahydronaphthyl, benzocycloheptanyl and benzocycloheptenyl, and fused heteroaryl selected from cyclopentenopyridine, cyclohexanopyridine, cyclopentanothiophene and cyclohexanothiophene, wherein the fused aryl or fused heteroaryl ring bears 0 to 3 groups selected from phenyl, naphthyl, heteroaryl selected from pyridinyl and thienyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, amino, mono- or di-($C_{1-3}$) alkylamino, phenylamino, naphthylamino, aminocarbonyl, mono- or di-($C_{1-3}$) alkylaminocarbonyl, amino($C_{1-5}$)alkyl or alkenyl, di-($C_{1-3}$)alkylamino($C_{1-5}$)alkyl or alkenyl, phenylamino($C_{1-3}$)alkyl or alkenyl, naphthylamino($C_{1-3}$)alkyl or alkenyl, phenylamido($C_{1-3}$)alkyl or alkenyl, naphthylamido($C_{1-3}$)alkyl or alkenyl, phenyl($C_{1-5}$)alkyl or alkenyl and naphthyl ($C_{1-5}$)alkyl or alkenyl;
c) cycloalkyl selected from cyclopentanyl, cyclohexanyl and cycloheptanyl, which cycloalkyl group is optionally partially or fully halogenated and which is optionally substituted with one to three $C_{1-3}$ alkyl groups;
d) cycloalkenyl selected from cyclopentenyl and cyclohexenyl, which cycloalkenyl group is optionally partially or fully halogenated and which is optionally substituted with one to three $C_{1-3}$ alkyl groups; and
e) phenyl($C_{1-5}$ branched or unbranched)alkyl, and naphthyl($C_{1-5}$ branched or unbranched)alkyl, wherein the phenyl or naphthyl ring is substituted with 0 to 5 groups selected from the group consisting of phenyl, naphthyl, heteroaryl selected from pyridinyl and thienyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy or heteroaryloxy wherein the heteroaryl moiety is as defined above in this subparagraph;

and $R_6$ is hydrogen, cyano or $C_{1-6}$ branched or unbranched alkyl which is optionally partially or fully halogenated.

3. A compound of the formula I according to claim 2, wherein:
the heterocyclic moiety

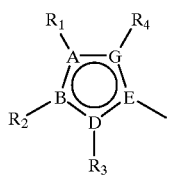

is

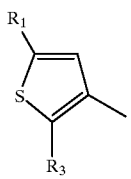

X is S or O;
Y is N—H;
$R_1$ is selected from the group consisting of:
a) $C_{3-7}$ branched alkyl, which is optionally partially or fully halogenated, and optionally substituted with one to three phenyl or heteroaryl independently selected from pyridinyl and thienyl, each phenyl or heteroaryl group being substituted with 0 to 3 groups selected from halogen, $C_{1-6}$ branched or unbranched alkyl which is optionally partially or fully halogenated, $C_{3-8}$ cycloalkyl and $C_{1-3}$ alkyloxy which is optionally partially or fully halogenated;
b) a cycloalkyl group selected from cyclopropyl, cyclobutyl, cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups;
c) $C_{3-7}$ branched alkenyl which is optionally partially or fully halogenated, and which is optionally substituted with one to three groups independently selected from $C_{1-5}$ branched or unbranched alkyl, phenyl or heteroaryl independently selected from pyridinyl and thienyl and each phenyl or heteroaryl group being substituted with 0 to 3 groups selected from halogen, $C_{1-6}$ branched or unbranched alkyl which is optionally partially or fully halogenated, cyclopropyl, cyclobutyl, cyclopentanyl and $C_{1-3}$ alkyloxy which is optionally partially or fully halogenated;
$R_3$ is selected from the group consisting of:
a) phenyl, naphthyl and heteroaryl selected from pyridinyl, quinolinyl and isoquinolinyl, wherein each phenyl, naphthyl or heteroaryl group is optionally substituted with one to three groups independently selected from $C_{1-6}$ branched or unbranched alkyl, phenyl, naphthyl, heteroaryl selected from the group set forth immediately above, $C_{1-6}$ branched or unbranched alkyl which is optionally partially or fully halogenated, cyclopropyl, cyclobutyl, cyclopentanyl, cyclohexanyl, halo, hydroxy, cyano, $C_{1-3}$ alkyloxy which is optionally partially or fully halogenated, phenyloxy, hetaryloxy wherein the heteroaryl moiety is selected from the group set forth above in this subparagraph, mono- or di-($C_{1-3}$) alkylamino, phenylamino, heteroarylamino wherein the heteroaryl moiety is selected from the group set forth above in this subparagraph, aminocarbonyl, a mono- or di-($C_{1-3}$)alkyl aminocarbonyl and mono- or di-($C_{1-3}$)alkylamino($C_{1-5}$)alkyl;
b) fused aryl selected from benzocyclobutanyl, indanyl, indenyl, dihydronaphthyl and tetrahydronaphthyl, and fused heteroaryl selected from cyclopentenopyridine, cyclohexanopyridine, cyclopentanothiophene and cyclohexanothiophene, wherein the fused aryl or fused heteroaryl ring is substituted with 0 to 3 groups independently selected from phenyl and heteroaryl selected from pyridinyl and thienyl, $C_{1-6}$ branched or unbranched alkyl which is optionally partially or fully halogenated, halo, cyano, $C_{1-3}$ alkyloxy which is optionally partially or fully halogenated, phenyloxy, heteroaryloxy wherein the heteroaryl moiety is selected from the group set forth above in this subparagraph, mono- or di-($C_{1-3}$)alkylamino, phenylamino, heteroarylamino wherein the heteroaryl moiety is selected from the group set forth above in this subparagraph, aminocarbonyl, a mono- or di-($C_{1-3}$)alkyl aminocarbonyl and mono- or di-($C_{1-3}$)alkylamino($C_{1-5}$)alkyl;

c) a cycloalkyl group selected from cyclopentanyl, cyclohexanyl and cycloheptanyl, which cycloalkyl group is optionally partially or fully halogenated and which is optionally substituted with one to three $C_{1-3}$ alkyl groups;

d) acetyl, benzoyl and phenylsulfonyl; and, $R_5$ is selected from the group consisting of:
a) phenyl, naphthyl and heteroaryl selected from pyridinyl, thienyl, quinolinyl and isoquinolinyl, wherein each phenyl, naphthyl or heteroaryl group optionally bears one to three groups selected from phenyl and heteroaryl wherein each heteroaryl moiety is independently selected from the group defined above in this subparagraph, $C_{1-6}$ branched or unbranched alkyl which is optionally partially or fully halogenated, cyclopropyl, cyclobutyl, cyclopentanyl, cyclohexanyl, halo, cyano, $C_{1-3}$ alkyloxy which is optionally partially or fully halogenated, phenyloxy, phenylamino;

b) fused aryl selected from benzocyclobutanyl, indanyl, indenyl, dihydronaphthyl, tetrahydronaphthyl, benzocycloheptanyl and benzocycloheptenyl, and fused heteroaryl selected from cyclopentenopyridine, cyclohexanopyridine, cyclopentanothiophene and cyclohexanothiophene, wherein the fused aryl or fused heteroaryl ring bears 0 to 3 groups selected from phenyl, $C_{1-6}$ branched or unbranched alkyl which is optionally partially or fully halogenated, halo, cyano, $C_{1-3}$ alkyloxy which is optionally partially or fully halogenated, phenyloxy and phenylamino; and c) phenyl($C_{1-5}$ branched or unbranched)alkyl, and naphthyl($C_{1-5}$ branched or unbranched)alkyl, wherein the phenyl or naphthyl ring is substituted with 0 to 3 groups selected from the group consisting of phenyl, $C_{1-6}$ branched or unbranched alkyl which is optionally partially or fully halogenated, halo, cyano, $C_{1-3}$ alkyloxy which is optionally partially or fully halogenated and phenyloxy.

4. A compound of the formula I according to claim 1, wherein:

the heterocyclic moiety

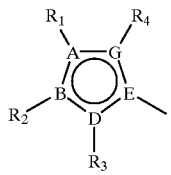

is

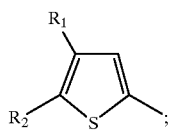

X is S or O;
Y is N—H;
$R_1$ is selected from the group consisting of:
a) $C_{3-10}$ branched alkyl, which is optionally partially or fully halogenated, and optionally substituted with one to three phenyl, naphthyl or heteroaryl groups independently selected from pyridinyl and thienyl, each such phenyl, naphthyl or heteroaryl group being substituted with 0 to 3 groups selected from halogen, $C_{1-6}$ branched or unbranched alkyl which is optionally partially or fully halogenated, $C_{3-8}$ cycloalkyl, hydroxy, cyano and $C_{1-3}$ alkyloxy which is optionally partially or fully halogenated;

b) a cycloalkyl group selected from cyclopropyl, cyclobutyl, cyclopentanyl, cyclohexanyl, cycloheptanyl, bicyclopentanyl, bicyclohexanyl and bicycloheptanyl, which cycloalkyl group is optionally partially or fully halogenated and which is optionally substituted with one to three $C_{1-3}$ alkyl groups, or an analog of such cycloalkyl group wherein instead of one to three ring methylene groups there are groups independently selected from O, S, CHOH, >C=O, >C=S and NH;

c) $C_{3-10}$ branched alkenyl which is optionally partially or fully halogenated, and which is optionally substituted with one to three groups independently selected from $C_{1-5}$ branched or unbranched alkyl, phenyl, naphthyl or heteroaryl independently selected from pyridinyl and thienyl and each such phenyl, naphthyl or heteroaryl group being substituted with 0 to 3 groups selected from halogen, $C_{1-6}$ branched or unbranched alkyl which is optionally partially or fully halogenated, cyclopropyl, cyclobutyl, cyclopentanyl, hydroxy, cyano, and $C_{1-3}$ alkyloxy which is optionally partially or fully halogenated;

d) a cycloalkenyl group selected from cyclopentenyl, cyclohexenyl, bicyclohexenyl and bicycloheptenyl, wherein such cycloalkenyl group is optionally substituted with one to three $C_{1-3}$ alkyl groups;

e) an alkoxy carbonyl group selected from methoxycarbonyl, ethoxycarbonyl and propoxycarbonyl;

$R_2$ is selected from the group consisting of: hydrogen, $C_{1-6}$ branched or unbranched alkyl which is optionally partially or fully halogenated, acetyl, benzoyl and phenylsulfonyl;

or $R_1$ and $R_2$ taken together optionally form a fused phenyl ring, $R_5$ is selected from the group consisting of:
a) phenyl, naphthyl and heteroaryl selected from pyridinyl, thienyl, quinolinyl, isoquinolinyl and indolyl, wherein such phenyl, naphthyl or heteroaryl group optionally bears one to three groups selected from phenyl, naphthyl and heteroaryl wherein each such heteroaryl moiety is independently selected from the group defined above in this subparagraph, $C_{1-6}$ branched or unbranched alkyl which is optionally partially or fully halogenated, cyclopropyl, cyclobutyl, cyclopentanyl, cyclohexanyl, halo, cyano, $C_{1-3}$ alkyloxy which is optionally partially or fully halogenated, phenyloxy, naphthyloxy, phenylamino, naphthylamino phenylamino($C_{1-3}$) alkyl or alkenyl, naphthylamino($C_{1-3}$)alkyl or alkenyl, phenylamido($C_{1-3}$)alkyl or alkenyl, naphthylamido($C_{1-3}$)alkyl or alkenyl, heteroarylamido($C_{1-3}$)alkyl or alkenyl wherein the heteroaryl moiety is as defined above in this subparagraph;

b) fused aryl selected from benzocyclobutanyl, indanyl, indenyl, dihydronaphthyl, tetrahydronaphthyl, benzocycloheptanyl and benzocycloheptenyl, and fused heteroaryl selected from cyclopentenopyridine, cyclohexanopyridine, cyclopentanothiophene and cyclohexanothiophene, wherein the fused aryl or fused heteroaryl ring bears 0 to 3 groups selected from phenyl, naphthyl, heteroaryl selected from pyridinyl and thienyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, phenylamino, naphthylamino, phenylamino($C_{1-3}$)alkyl or alkenyl, naphthylamino($C_{1-3}$)alkyl or alkenyl, phenylamido($C_{1-3}$)alkyl or alkenyl, naphthylamido($C_{1-3}$)alkyl or alkenyl, heteroarylamido($C_{1-3}$)alkyl or alkenyl wherein the heteroaryl moiety is as defined above in this subparagraph; and c) phenyl($C_{1-5}$ branched or unbranched)alkyl, and naphthyl($C_{1-5}$ branched or unbranched)alkyl, wherein the phenyl or naphthyl ring is substituted with 0 to 3 groups selected from the group consisting of phenyl, naphthyl, heteroaryl selected from pyridinyl and thienyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy or heteroaryloxy wherein the heteroaryl moiety is as defined above in this subparagraph.

5. A pharmaceutical composition comprising a compound according to claim 1 and a pharmaceutically acceptable carrier.

6. A method for treating a disease or pathological condition involving inflammation comprising administering to a host in need of such treatment a therapeutically effective amount of a compound in accordance with claim 1.

7. The method according to claim 6 wherein the pathological condition is a chronic inflammatory disease.

8. The method according to claim 6 wherein the pathological condition is an acute inflammatory disease.

9. A method of reducing undesirable levels of one or more of the cytokines TNFα, IL-1β, GM-CSF, IL-6, or IL-8 comprising administering to a host a therapeutically effective amount of a compound in accordance with claim 1.

10. A compound of the formula(I) according to claim 1

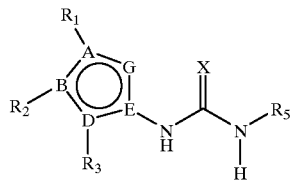

(I)

wherein the heterocyclic moiety:

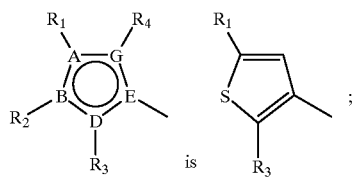

is and $R_1$, $R_3$, $R_5$ and X are selected from:

| $R_1$ | $R_3$ | $R_5$ | X | |
|---|---|---|---|---|
| t-butyl | Phenyl | 4-chloro-phenyl | O | ; |
| t-butyl | Phenyl | 2-indanyl | O | and |
| 1-methyl-cyclopent-1-yl | Pyridin-3-yl | 1-naphthyl | O | . | or a tautomer or pharmaceutically acceptable salt thereof.

11. A method treating a disease selected from the group consisting of adult respiratory distress syndrome (ARDS), Alzheimer's disease, Crohn's disease, type I diabetes, type II diabetes, graft vs. host reaction, inflammatory bowel disease, multiple sclerosis, myocardial infarction, osteoarthritis, osteoporosis, psoriasis, rheumatoid arthritis, stroke, sepsis, septic shock, toxic shock syndrome and ulcerative colitis, comprising administering to a host in need of such treatment a therapeutically effective amount of a compound in accordance with claim 1.

* * * * *